United States Patent [19]

Kleefeld et al.

[11] Patent Number: 4,962,118
[45] Date of Patent: Oct. 9, 1990

[54] FUNGICIDAL SUBSTITUTED TRIAZOLES

[75] Inventors: Gerd Kleefeld; Stefan Dutzmann, both of Duesseldorf, Fed. Rep. of Germany

[73] Assignee: Bayer Aktiengesellschaft, Leverkusen, Fed. Rep. of Germany

[21] Appl. No.: 311,327

[22] Filed: Feb. 15, 1989

[30] Foreign Application Priority Data

Feb. 18, 1988 [DE] Fed. Rep. of Germany ....... 3804981

[51] Int. Cl.$^5$ ................. A01N 43/653; C07D 249/08
[52] U.S. Cl. .................................... 514/383; 514/184; 548/101; 548/267.4
[58] Field of Search ..................... 548/101, 262, 267.4; 514/184, 383

[56] References Cited

U.S. PATENT DOCUMENTS

| | | | |
|---|---|---|---|
| 4,451,281 | 5/1984 | Elbe et al. | 548/262 |
| 4,622,335 | 11/1986 | Kramer et al. | 548/262 |
| 4,772,623 | 9/1988 | Timmler et al. | 514/383 |
| 4,843,088 | 6/1989 | Holmwood et al. | 548/262 |

Primary Examiner—Glennon H. Hollrah
Assistant Examiner—Patricia L. Morris
Attorney, Agent, or Firm—Sprung, Horn Kramer & Woods

[57] ABSTRACT

Fungicidal trazoles of the formula

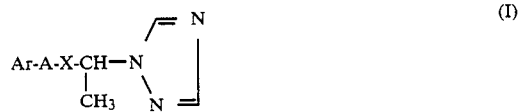

in which
Ar stands for optionally substituted aryl,
A stands for the groups

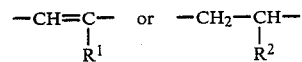

and
X stands for the groups

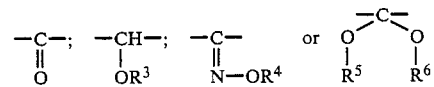

wherein
$R^1$ stands for hydrogen or alkyl,
$R^2$ stands for hydrogen or alkyl,
$R^3$ stands for hydrogen, alkyl, alkenyl, alkanoyl, for optionally substituted cycloalkyl or for in each case optionally substituted aralkyl or aroyl,
$R^4$ stands for hydrogen, alkyl, for optionally substituted cycloalkyl or for in each case optionally substituted aralkyl or aryl and
$R^5$ and $R^6$ independently of one another stand for alkyl or for optionally substituted aralkyl or together stand for an optionally substituted doubly-linked alkylene radical, and addition products thereof with acids and metal salts.

9 Claims, No Drawings

FUNGICIDAL SUBSTITUTED TRIAZOLES

The invention relates to new substituted triazoles, several processes for their preparation and their use as fungicides.

It has already been disclosed that certain substituted triazoles possess a fungicidal activity (cf. DE-OS (German Published Specification) No. 2,431,407). Thus, for example 1-(4-chlorophenyl)-2-(1,2,4-triazol-1-yl)-propan-1-ol and 1-(4-chlorophenyl)-2-(1,2,4-triazol-1-yl)-propan-1-one can be used for combating fungi. However, the activity of these substances is not completely satisfactory in all fields of application, in particular at lower application rates and when low concentrations are applied.

New substituted triazoles of the formula $$Ar\text{-}A\text{-}X\text{-}CH(CH_3)\text{-}N\diagup\!\!\!\diagdown\text{ (triazole)} \quad (I)$$

in which
- Ar stands for optionally substituted aryl,
- A stands for the groups $$-CH=C(R^1)-\ \text{or}\ -CH_2-CH(R^2)-$$

and X stands for the groups $$-\underset{O}{\overset{\parallel}{C}}-;\ -\underset{OR^3}{\overset{|}{CH}}-;\ -\underset{N-OR^4}{\overset{\parallel}{C}}-\ \text{or}\ \underset{R^5\ R^6}{\overset{\diagup C\diagdown}{O\ \ \ O}}$$

wherein
- $R^1$ stands for hydrogen or alkyl,
- $R^2$ stands for hydrogen or alkyl,
- $R^3$ stands for hydrogen, alkyl, alkenyl, alkanoyl, for optionally substituted cycloalkyl or for in each case optionally substituted aralkyl or aroyl,
- $R^4$ stands for hydrogen, alkyl, for optionally substituted cycloalkyl or for in each case optionally substituted aralkyl or aryl and
- $R^5$ and $R^6$ independently of one another stand for alkyl or for optionally substituted aralkyl or together stand for an optionally substituted doubly-linked alkylene radical, and their acid addition salts and metal salt complexes have been found.

The compounds of the formula (I) contain at least one asymmetrically substituted carbon atom. Thus, they can be present in the form of optically active compounds. In addition, those compounds in which A stands for a $-CH=CR^1-$ group can be present in the form of geometrical isomers. The present invention relates both to the pure isomers and also isomer mixtures.

Furthermore, it has been found that the new substituted triazoles of the formula (I) and their acid addition salts and metal salt complexes can be prepared by a plurality of processes.

Thus,
(a) substituted triazoles of the formula $$Ar-CH=C(R^1)-\underset{O}{\overset{\parallel}{C}}-CH(CH_3)-N\diagup\!\!\!\diagdown \quad (Ia)$$

in which
Ar and $R^1$ have the abovementioned meaning, are obtained when aromatic aldehydes of the formula $$Ar-\underset{O}{\overset{\parallel}{C}}-H \quad (II)$$

in which
Ar has the abovementioned meaning are reacted with triazolylketones of the formula $$R^1-CH_2-\underset{O}{\overset{\parallel}{C}}-CH(CH_3)-N\diagup\!\!\!\diagdown \quad (III)$$

in which
$R^1$ has the abovementioned meaning if appropriate in the presence of a diluent and if appropriate in the presence of a reaction auxiliary; (b) substituted triazoles of the formula $$Ar-CH_2-CH(R^2)-X^1-CH(CH_3)-N\diagup\!\!\!\diagdown \quad (Ib)$$

in which
$X^1$ stands for one of the groups $$-\underset{O}{\overset{\parallel}{C}}-\ \text{or}\ -\underset{OH}{\overset{|}{CH}}-,$$

and
Ar and $R^2$ have the abovementioned meaning, are obtained when substituted triazoles of the formula $$Ar-CH=C(R^1)-\underset{O}{\overset{\parallel}{C}}-CH(CH_3)-N\diagup\!\!\!\diagdown \quad (Ia)$$

in which
Ar and $R^1$ have the abovementioned meaning, are hydrogenated with hydrogen in the presence of a hydrogenation catalyst and in the presence of a diluent;

(c) substituted triazoles of the formula $$Ar-CH=C(R^1)-\underset{OH}{\overset{|}{CH}}-CH(CH_3)-N\diagup\!\!\!\diagdown \quad (Ic)$$

in which
Ar and $R^1$ have the abovementioned meaning, are obtained when substituted triazoles of the formula

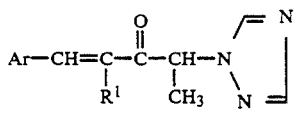 (Ia)

in which

Ar and R¹ have the abovementioned meaning, are reduced with complex hydrides in the presence of a diluent;

(d) substituted triazoles of the formula

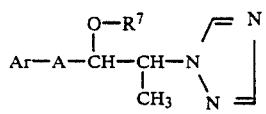 (Id)

in which

R⁷ stands for alkyl, alkenyl, alkanoyl, for optionally substituted cycloalkyl or for in each case optionally substituted aralkyl or aroyl, and Ar and A have the abovementioned meaning, are obtained when substituted triazoles of the formula

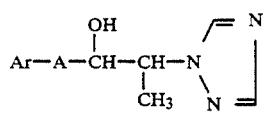 (Ie)

in which

Ar and A have the abovementioned meaning, are reacted with compounds of the formula

    (IV)

in which

R⁷ has the abovementioned meaning, and

E stands for an electron-withdrawing leaving group, if appropriate in the presence of a diluent and if appropriate in the presence of a reaction auxiliary;

(e) substituted triazoles of the formula

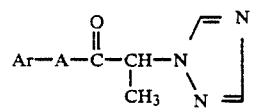 (If)

in which

Ar and A have the abovementioned meaning are obtained when substituted triazoles of the formula

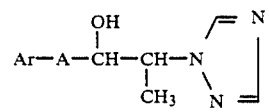 (Ie)

in which

Ar and A have the abovementioned meaning are reacted with an oxidizing agent if appropriate in the presence of a diluent;

(f) substituted triazoles of the formula

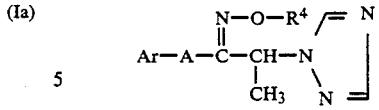 (Ig)

in which

Ar, A and R⁴ have the abovementioned meaning, are obtained when substituted triazoles of the formula

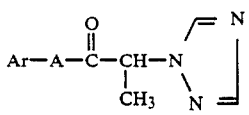 (If)

in which

Ar and A have the abovementioned meaning are reacted with hydroxylamine derivatives of the formula $$H_2N-O-R^4 \qquad (V)$$

in which

R⁴ has the abovementioned meaning, or with their acid addition salts if appropriate in the presence of a diluent and if appropriate in the presence of a reaction auxiliary;

(g) substituted triazoles of the formula

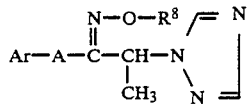 (Ih)

in which

Ar and A have the abovementioned meaning, and

R⁸ stands for alkyl, for optionally substituted cycloalkyl or for optionally substituted aralkyl are obtained when substituted triazoles of the formula

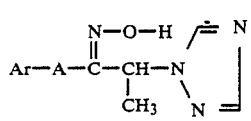 (Ii)

in which

Ar and A have the abovementioned meaning, are reacted with compounds of the formula $$R^8-E^1 \qquad (VI)$$

in which

R⁸ has the abovementioned meaning, and

E¹ stands for an electron-withdrawing leaving group, if appropriate in the presence of a diluent and if appropriate in the presence of a reaction auxiliary;

(h) substituted triazoles of the formula

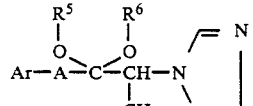 (Ij)

in which

Ar, A, $R^5$ and $R^6$ have the abovementioned meaning, are obtained when substituted triazoles of the formula $$Ar-A-\overset{O}{\underset{\underset{CH_3}{|}}{\overset{\|}{C}}}-\overset{}{\underset{}{CH}}-N\diagup\!\!\!\diagdown_{N}^{\!\!=\!\!N} \qquad (If)$$

in which

Ar and A have the abovementioned meaning, are reacted either (α) with alcohols of the formulae $R^5$—OH(VII) or $R^6$—OH      (VIII)

in which $R^5$ and $R^6$ each stand for alkyl or for optionally substituted aralkyl, or (β) with diols of the formula $$Y\diagup\!\!\!\!\diagdown_{OH}^{OH} \qquad (IX)$$

in which

Y stands for optionally substituted alkylene, if appropriate in the presence of a diluent and if appropriate in the presence of a reaction auxiliary, and when, if desired, an acid or a metal salt is subjected to an addition reaction with the resulting substituted triazoles of the formula (I).

Finally, it has been found that the new substituted triazoles of the formula (I) and their acid addition salts and metal salt complexes possess a good fungicidal activity.

Surprisingly, the substances according to the invention show a considerably better fungicidal activity than 1-(4-chlorophenyl)-2-(1,2,4-triazol-1-yl)-propan1-ol and 1-(4-chlorophenyl)-2-(1,2,4-triazol-1-yl)-propan-1-one, which are chemically similar compounds of a similar type of action known from the prior art.

Formula (I) provides a general definition of the substituted triazoles according to the invention. Preferred compounds of the formula (I) are those in which Ar stands for aryl which has 6 to 10 carbon atoms and which can be monosubstituted or polysubstituted by identical or different substituents from the series comprising halogen, cyano, nitro, in each case straight-chain or branched alkyl, alkoxy and alkylthio, each having 1 to 4 carbon atoms, in each case straight-chain or branched halogenoalkyl, halogenoalkoxy and halogenoalkylthio, each having 1 to 4 carbon atoms and 1 to 9 identical or different halogen atoms, in each case straight-chain or branched alkoxycarbonyl and alkoximinoalkyl, each having 1 to 4 carbon atoms in the alkoxy moiety and 1 to 4 carbon atoms in the alkyl moiety, phenyl which is optionally monosubstituted or polysubstituted by identical or different substituents from the series comprising halogen and/or straight-chain or branched alkyl having 1 to 4 carbon atoms, phenoxy which is optionally monosubstituted or polysubstituted by identical or different substituents from the series comprising halogen and/or straight-chain or branched alkyl having 1 to 4 carbon atoms and/or by benzyloxy which is optionally monosubstituted or polysubstituted by identical or different substituents from the series comprising halogen and/or straight-chain or branched alkyl having 1 to 4 carbon atoms, A stands for the group $$-CH=C- \quad \text{or} \quad -CH_2-CH- \\ \phantom{-CH=}|\phantom{C-} \qquad \phantom{-CH_2-}|\phantom{CH-} \\ \phantom{-CH=}R^1\phantom{C-} \qquad \phantom{-CH_2-}R^2\phantom{CH-}$$

and

X stands for the groups $$-\underset{\underset{O}{\|}}{C}-; \quad \underset{\underset{O-R^3}{|}}{CH}-; \quad -\underset{\underset{N-O-R^4}{\|}}{C}- \quad \text{or} \quad O\diagup\!\!\!\overset{-C-}{\diagdown}\!\!O \\ \phantom{xxxxxxxxxxxxxxxxxxxxxxxxxx} R^5 \phantom{x} R^6$$

where $R^1$ stands for hydrogen or for straight-chain or branched alkyl having 1 to 4 carbon atoms, $R^2$ stands for hydrogen or straight-chain or branched alkyl having 1 to 4 carbon atoms, $R^3$ stands for hydrogen, for in each case straight-chain or branched alkyl having 1 to 8 carbon atoms, alkenyl having 3 to 8 carbon atoms or alkanoyl having 1 to 6 carbon atoms in the alkane moiety, furthermore stands for cycloalkyl which has 3 to 7 carbon atoms and which can be monosubstituted or polysubstituted by identical or different substituents from the series comprising halogen, straight-chain or branched alkyl having 1 to 4 carbon atoms and/or straight-chain or branched halogenoalkyl having 1 to 4 carbon atoms and 1 to 9 identical or different halogen atoms, or stands for aralkyl having 6 to 10 carbon atoms in the aryl moiety and 1 to 4 carbon atoms in the straight-chain or branched alkyl moiety, it being possible for each of the radicals to be monosubstituted or polysubstituted in the aryl moiety by identical or different substituents from the series comprising halogen, cyano, nitro, in each case straight-chain or branched alkyl, alkoxy or alkylthio, each having 1 to 4 carbon atoms and/or in each case straight-chain or branched halogenoalkyl, halogenoalkoxy or halogenoalkylthio, each having 1 to 4 carbon atoms and 1 to 9 identical or different halogen atoms, or stands for aroyl having 6 to 10 carbon atoms in the aryl moiety, it being possible for each of these aryl radicals to be monosubstituted or polysubstituted by identical or different substituents from the series comprising halogen, cyano, nitro, in each case straight-chain or branched alkyl, alkoxy or alkylthio, each having 1 to 4 carbon atoms and/or in each case straight-chain or branched halogenoalkyl, halogenoalkoxy or halogenoalkylthio, each having 1 to 4 carbon atoms and 1 to 9 identical or different halogen atoms, $R^4$ stands for hydrogen, straight-chain or branched alkyl having 1 to 6 carbon atoms or stands for cycloalkyl having 3 to 7 carbon atoms, it being possible for each of the cycloalkyl radicals to be monosubstituted or polysubstituted by identical or different substituents from the series comprising halogen, straight-chain or branched alkyl having 1 to 4 carbon atoms and/or straight-chain or branched halogenoalkyl having 1 to 4 carbon atoms and 1 to 9 identical or different halogen atoms, or stands for aralkyl having 6 to 10 carbon atoms in the aryl moiety and 1 to 4 carbon atoms in the straight-chain or branched alkyl moiety, it being possible for each of the alkyl radicals to be monosubstituted or polysubstituted by identical or different substituents from the series comprising halogen, cyano, nitro, in each case straight-chain or branched alkyl, alkoxy or alkylthio, each having 1 to 4 carbon atoms, in each case straight-chain or branched halogenoalkyl, halogenoalkoxy and/or halogenoalkylthio, each having 1 to 4 carbon atoms and 1 to 9 identical or different halogen atoms, or stands for aryl having 6 to 10 carbon atoms, it being possible for each of the aryl radicals to be monosubstituted or polysubstituted by identical or different substituents from the series comprising halogen, cyano, nitro, in each case straight-chain or branched alkyl, alkoxy or alkylthio, each having 1 to 4 carbon atoms, in each case straight-chain or branched halogenoalkyl, halogenoalkoxy and/or halogenoalkylthio, each having 1 to 4 carbon atoms and 1 to 9 identical or different halogen atoms and $R^5$ and $R^6$ independently of one another stand for alkyl having 1 to 6 carbon atoms or aralkyl having 6 to 10 carbon atoms in the aryl moiety and 1 to 4 carbon atoms in the straight-chain or branched alkyl moiety, it being possible for each of the aryl radicals to be monosubstituted or polysubstituted by identical or different substituents from the series comprising halogen, cyano, nitro, in each case straight-chain or branched alkyl, alkoxy or alkylthio, each having 1 to 4 carbon atoms, in each case straight-chain or branched halogenoalkyl, halogenoalkoxy and/or halogenoalkylthio, each having 1 to 4 carbon atoms and 1 to 9 identical or different halogen atoms, or $R^5$ and $R^6$ together stand for an alkylene radical having 2 to 4 carbon atoms, it being possible for the alkylene radical to be monosubstituted or polysubstituted by identical or different substituents from the series comprising straight-chain or branched alkyl having 1 to 4 carbon atoms, straight-chain or branched halogenoalkyl having 1 to 4 carbon atoms and 1 to 9 identical or different halogen atoms, alkoxyalkyl having 1 to 4 carbon atoms in the alkyl moiety and 1 to 4 carbon atoms in the alkoxy moiety and/or aralkyloxyalkyl having 6 to 10 carbon atoms in the aryl moiety and 1 to 4 carbon atoms in the straight-chain or branched alkyloxy moiety and also 1 to 4 carbon atoms in the straight-chain or branched alkyl moiety, it being possible for the aryl radical to be monosubstituted or polysubstituted by identical or different substituents from the series comprising halogen and/or alkyl having 1 to 4 carbon atoms.

Particularly preferred compounds of the formula (I) are those in which

Ar stands for phenyl which can be monosubstituted, disubstituted or trisubstituted by identical or different substituents from the series comprising fluorine, chlorine, bromine, cyano, nitro, methyl, ethyl, n- or i-propyl, n-, i-, s- or t-butyl, methoxy, ethoxy, n- or i-propoxy, methylthio, trifluoromethyl, difluoromethyl, fluorochloromethyl, difluorochloromethyl, trifluoromethoxy, difluoromethoxy, fluorochloromethoxy, difluorochloromethoxy, trifluoromethylthio, methoxycarbonyl, ethoxycarbonyl, methoximinomethyl, ethoximinomethyl, methoximinoethyl, ethoximinoethyl, phenyl which is optionally monosubstituted, disubstituted or trisubstituted by identical or different substituents from the series comprising fluorine, chlorine, bromine, methyl and/or ethyl, phenoxy which is optionally monosubstituted, disubstituted or trisubstituted by identical or different substituents from the series comprising fluorine, chlorine, bromine, methyl and/or ethyl, and/or benzyloxy which is optionally monosubstituted, disubstituted or trisubstituted by identical or different substituents from the series comprising fluorine, chlorine, bromine, methyl and/or ethyl, A stands for the groups

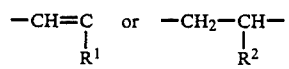

and

X stands for the groups

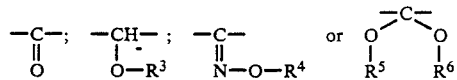

where $R^1$ stands for hydrogen, methyl, ethyl, n- or i-propyl and also n-, i-, s- or t-butyl, $R^2$ stands for hydrogen, methyl, ethyl, n- or i-propyl and also n-, i-, s- or t-butyl, $R^3$ stands for hydrogen, methyl, ethyl, n- or i-propyl, n-, i-, s- or t-butyl, for allyl, for straight-chain or branched butenyl, for formyl, acetyl or propionyl, furthermore stands for cyclopropyl, cyclopentyl or cyclohexyl, each of which is optionally monosubstituted, disubstituted or trisubstituted by identical or different substituents from the series comprising fluorine, chlorine, bromine, methyl, ethyl and/or trifluoromethyl, and furthermore stands for benzyl, phenethyl or benzoyl, it being possible for each of the three abovementioned radicals to be monosubstituted, disubstituted or trisubstituted in the phenyl moiety by identical or different substituents from the series comprising fluorine, chlorine, bromine, cyano, nitro, methyl, ethyl, n- or i-propyl, n-, i-, s- or t-butyl methoxy, ethoxy, n- or i-propoxy, methylthio, trifluoromethyl, trifluoromethoxy and/or trifluoromethylthio, $R^4$ stands for hydrogen, methyl, ethyl, n- or i-propyl, n-, i-, s- or t-butyl, furthermore stands for cyclopropyl, cyclopentyl or cyclohexyl, each of which is optionally monosubstituted, disubstituted or trisubstituted by identical or different substituents from the series comprising fluorine, chlorine, bromine, methyl, ethyl and/or trifluoromethyl, and furthermore stands for benzyl, phenethyl or phenyl, it being possible for each of the three abovementioned radicals to be monosubstituted, disubstituted or trisubstituted in the phenyl moiety by identical or different substituents from the series comprising fluorine, chlorine, bromine, cyano, nitro, methyl, ethyl, n- or i-propyl, n-, i-, s- or t-butyl, methoxy, ethoxy, n- or i-propoxy, methylthio, trifluoromethyl, trifluoromethoxy and/or trifluoromethylthio, and $R^5$ and $R^6$ each stand for methyl, ethyl or benzyl, it being possible for the benzyl radical to be monosubstituted, disubstituted or trisubstituted in the phenyl moiety by identical or different substituents from the series comprising fluorine, chlorine, bromine, cyano, nitro, methyl, ethyl, n- or i-propyl, n-, i-, s- or t-butyl, methoxy, ethoxy, n- or i-propoxy, methylthio, trifluoromethyl, trifluoromethoxy or trifluoromethylthio, or $R^5$ and $R^6$ together stand for a 1,2-ethanediyl radical which can be monosubstituted to tetrasubstituted by identical or different substituents from the series comprising methyl, ethyl, n- or i-propyl, n-butyl, chloromethyl, trifluoromethyl, methoxymethyl, ethoxymethyl, methoxyethyl, ethoxyethyl and/or benzyloxymethyl which is optionally monosubstituted, disubstituted or trisubstituted in the phenyl moiety by identical or different substituents from the series comprising fluorine, chlorine, bromine, methyl and/or ethyl.

Other preferred compounds according to the invention are addition products of acids and those substituted triazoles of the formula (I) in which the substituents Ar, A and X have the meanings which have already been preferably mentioned for these substituents.

Acids which can be subjected to the addition reaction preferably include hydrohalic acids, such as, for example, hydrochloric acid and hydrobromic acid, in particular hydrochloric acid, furthermore phosphoric acid, nitric acid, sulphuric acid, mono-, bi- and trifunctional carboxylic acids and hydroxycarboxylic acids, such as, for example, acetic acid, maleic acid, succinic acid, fumaric acid, tartaric acid, citric acid, salicylic acid, sorbic acid and lactic acid, sulphonic acids, such as, for example, p-toluenesulphonic acid and 1,5-naphthalenedisulphonic acid, and also saccharin or thiosaccharin.

Other preferred compounds according to the invention are addition products of salts of metals of main groups II to IV and of subgroups I and II and also IV to VIII of the Periodic Table of the Elements and those substituted triazoles of the formula (I) in which the substituents Ar, A and X have the meanings which have already been preferably mentioned for these substituents.

Of these, particularly preferred salts are those of copper, zinc, manganese, magnesium, tin, iron and nickel. Suitable anions of these salts are those which are derived from those acids which give addition products tolerated by plants. Particularly preferred acids of this type are in this context the hydrohalic acids, such as, for example, hydrochloric acid and hydrobromic acid, nitric acid and sulphuric acid.

Very particularly preferred compounds of the formula (I) are those in which

Ar stands for phenyl which can be monosubstituted or disubstituted by identical or different substituents from the series comprising fluorine, chlorine, bromine, cyano, methyl, ethyl, n- or i-propyl, n-, i-, s- or t-butyl, methoxy, ethoxy, n- or i-propoxy, methylthio, trifluoromethyl, difluoromethyl, fluorochloromethyl, difluorochloromethyl, trifluoromethoxy, difluoromethoxy, fluorochloromethoxy, difluorochloromethoxy, trifluoromethylthio, methoximinomethyl, ethoximinomethyl, methoximinoethyl and ethoximinoethyl, phenyl which is optionally monosubstituted or disubstituted by chlorine, phenoxy which is optionally monosubstituted or disubstituted by chlorine or by benzyloxy which is optionally monosubstituted or disubstituted by chlorine, A stands for the groups

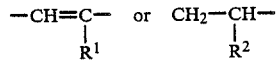

and

X stands for the groups

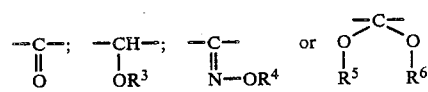

where
$R^1$ stands for hydrogen or methyl,
$R^2$ stands for hydrogen or methyl,
$R^3$ stands for hydrogen, methyl, ethyl, allyl, acetyl, propionyl, for cyclohexyl, for benzyl or benzoyl which are substituted by identical or different substituents from the series comprising fluorine, chlorine and/or trifluoromethoxy,
$R^4$ stands for hydrogen, methyl, ethyl, cyclohexyl, for benzyl, phenethyl or phenyl which are optionally monosubstituted or disubstituted by chlorine or nitro, and
$R^5$ and $R^6$ each stand for methyl, ethyl or benzyl or together stand for a 1,2-ethanediyl radical which is optionally substituted by methyl or chloromethyl.

The following substituted triazoles of the general formula (I) may be mentioned individually in addition to the compounds mentioned in the preparation examples:

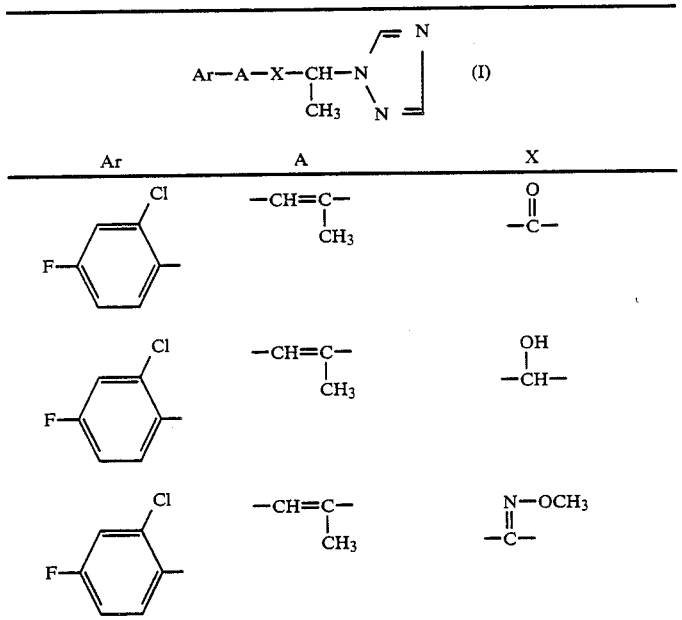

-continued $$Ar-A-X-\underset{\underset{CH_3}{|}}{CH}-N\overset{N}{\underset{N}{\diagdown}}\diagup \qquad (I)$$

| Ar | A | X |
|---|---|---|
| 2-Cl, 4-F-phenyl | -CH₂-CH(CH₃)- | -C(=O)- |
| 2-Cl, 4-F-phenyl | -CH₂-CH(CH₃)- | -CH(OH)- |
| 2-Cl, 4-F-phenyl | -CH₂-CH(CH₃)- | -C(=N-OCH₃)- |
| 2-Cl, 4-F-phenyl | -CH₂-CH(CH₃)- | -CH(O-CH₂-(2,4-diCl-phenyl))- |
| 4-Cl-phenyl | -CH₂-CH(CH₃)- | -CH(O-CH₂-(4-OCF₃-phenyl))- |
| 2,4-diCl-phenyl | -CH₂-CH(CH₃)- | -CH(O-CH₂-(4-F-phenyl))- |
| 2,4-diF-phenyl | -CH=C(CH₃)- | -C(=O)- |
| 2,4-diF-phenyl | -CH=C(CH₃)- | -CH(OH)- |
| 2,4-diF-phenyl | -CH=C(CH₃)- | -C(=N-OCH₃)- |
| 2,4-diF-phenyl | -CH₂-CH(CH₃)- | -C(=O)- |

-continued $$Ar-A-X-CH-N\begin{smallmatrix}&\\&\\CH_3\end{smallmatrix}\begin{smallmatrix}N\\ \diagdown\\ N\end{smallmatrix}\begin{smallmatrix}\diagup\hspace{-2pt}=\hspace{-2pt}N\\ \\ \diagdown\hspace{-2pt}=\hspace{-2pt}N\end{smallmatrix}\qquad (I)$$

| Ar | A | X |
|---|---|---|
| 2,4-difluorophenyl | −CH₂−CH(CH₃)− | −CH(OH)− |
| 2,4-difluorophenyl | −CH₂−CH(CH₃)− | −C(=N−OCH₃)− |
| 2,4-difluorophenyl | −CH₂−CH(CH₃)− | −CH(O−CH₂−(4-chlorophenyl))− |
| 2,4-difluorophenyl | −CH₂−CH(CH₃)− | −CH(O−CH₂−(2,4-dichlorophenyl))− |
| 2,4-difluorophenyl | −CH₂−CH(CH₃)− | −CH(O−CH₂−phenyl)− |
| 2,4-difluorophenyl | −CH₂−CH(CH₃)− | cyclic -C(CH₃)(O-CH₂-CH₂-O)- (1,3-dioxolane) |
| 3,4-dichlorophenyl | −CH=C(CH₃)− | −C(=O)− |
| 3,4-dichlorophenyl | −CH=C(CH₃)− | −CH(OH)− |
| 3,4-dichlorophenyl | −CH=C(CH₃)− | −C(=N−OCH₃)− |
| 3,4-dichlorophenyl | −CH₂−CH(CH₃)− | −C(=O)− |

-continued $$Ar-A-X-CH-N\underset{\underset{N}{|}}{\overset{\overset{N}{\nearrow}}{\diagdown}}\quad (I)$$
$$\underset{CH_3}{|}$$

| Ar | A | X |
|---|---|---|
| 3,4-diClC₆H₃— | —CH₂—CH(CH₃)— | —CH(OH)— |
| 3,4-diClC₆H₃— | —CH₂—CH(CH₃)— | —C(=N—OCH₃)— |
| 3,4-diClC₆H₃— | —CH₂—CH(CH₃)— | —CH(O—CH₂—C₆H₄-4-Cl)— |
| 3,4-diClC₆H₃— | —CH₂—CH(CH₃)— | —CH(O—CH₂—C₆H₃-2,4-diCl)— |
| 3,4-diClC₆H₃— | —CH₂—CH(CH₃)— | —CH(O—CH₂—C₆H₅)— |
| 3,4-diClC₆H₃— | —CH₂—CH(CH₃)— | cyclic methyl orthoester (1,3-dioxolane) |
| 4-F₃CS—C₆H₄— | —CH=C(CH₃)— | —C(=O)— |
| 4-F₃CS—C₆H₄— | —CH=C(CH₃)— | —CH(OH)— |
| 4-F₃CS—C₆H₄— | —CH=C(CH₃)— | —C(=N—OCH₃)— |
| 4-F₃CS—C₆H₄— | —CH₂—CH(CH₃)— | —C(=O)— |
| 4-F₃CS—C₆H₄— | —CH₂—CH(CH₃)— | —CH(OH)— |

-continued $$Ar-A-X-CH-N\underset{CH_3}{\overset{}{|}}\diagdown\underset{N}{\overset{N}{\diagup}}\diagdown \quad (I)$$

| Ar | A | X |
|---|---|---|
| F₃CS–C₆H₄– | –CH₂–CH(CH₃)– | –C(=N–OCH₃)– |
| F₃CS–C₆H₄– | –CH₂–CH(CH₃)– | –CH(O–CH₂–C₆H₄–Cl)– |
| F₃CS–C₆H₄– | –CH₂–CH(CH₃)– | –CH(O–CH₂–(2,4-Cl₂C₆H₃))– |
| F₃CS–C₆H₄– | –CH₂–CH(CH₃)– | –CH(O–CH₂–C₆H₅)– |
| F₃CS–C₆H₄– | –CH₂–CH(CH₃)– | 2,2-dimethyl-1,3-dioxolane |
| F–C₆H₄– | –CH=C(CH₃)– | –C(=O)– |
| F–C₆H₄– | –CH=C(CH₃)– | –CH(OH)– |
| F–C₆H₄– | –CH=C(CH₃)– | –C(=N–OCH₃)– |
| F–C₆H₄– | –CH₂–CH(CH₃)– | –C(=O)– |
| F–C₆H₄– | –CH₂–CH(CH₃)– | –CH(OH)– |
| F–C₆H₄– | –CH₂–CH(CH₃)– | –C(=N–OCH₃)– |
| F–C₆H₄– | –CH₂–CH(CH₃)– | –CH(O–CH₂–C₆H₄–Cl)– |

-continued $$\text{Ar}-\text{A}-\text{X}-\underset{\underset{\text{CH}_3}{|}}{\text{CH}}-\text{N}\underset{\text{N}}{\overset{\text{N}}{\diagdown}}\diagup \quad \text{(I)}$$

| Ar | A | X |
|---|---|---|
| 4-F-C₆H₄- | -CH₂-CH(CH₃)- | -CH(O-CH₂-(2,4-Cl₂-C₆H₃))- |
| 4-F-C₆H₄- | -CH₂-CH(CH₃)- | -CH(O-CH₂-C₆H₅)- |
| 4-F-C₆H₄- | -CH₂-CH(CH₃)- | 2,2-dimethyl-1,3-dioxolan-4-yl (spiro -O-C(CH₃)₂-O-CH₂-) |
| 4-F, 3-C₆H₅O-C₆H₃- | -CH=C(CH₃)- | -C(=O)- |
| 4-F, 3-C₆H₅O-C₆H₃- | -CH=C(CH₃)- | -CH(OH)- |
| 4-F, 3-C₆H₅O-C₆H₃- | -CH=C(CH₃)- | -C(=N-OCH₃)- |
| 4-F, 3-C₆H₅O-C₆H₃- | -CH₂-CH(CH₃)- | -C(=O)- |
| 4-F, 3-C₆H₅O-C₆H₃- | -CH₂-CH(CH₃)- | -CH(OH)- |
| 4-F, 3-C₆H₅O-C₆H₃- | -CH₂-CH(CH₃)- | -C(=N-OCH₃)- |
| 4-F, 3-C₆H₅O-C₆H₃- | -CH₂-CH(CH₃)- | -CH(O-CH₂-(4-Cl-C₆H₄))- |

-continued $$Ar-A-X-CH-N \begin{array}{c} N \\ \diagup \\ \diagdown \\ N \end{array} \quad (I)$$
$$\phantom{Ar-A-X-}CH_3$$

| Ar | A | X |
|---|---|---|
| 2-C₆H₅O, 4-F-C₆H₃- | -CH₂-CH(CH₃)- | -CH(O-CH₂-(2,4-Cl₂-C₆H₃))- |
| 2-C₆H₅O, 4-F-C₆H₃- | -CH₂-CH(CH₃)- | -CH(O-CH₂-C₆H₅)- |
| 2-C₆H₅O, 4-F-C₆H₃- | -CH₂-CH(CH₃)- | 2-methyl-1,3-dioxolan-2-yl |
| 4-F₃C-C₆H₄- | -CH=C(CH₃)- | -C(=O)- |
| 4-F₃C-C₆H₄- | -CH=C(CH₃)- | -CH(OH)- |
| 4-F₃C-C₆H₄- | -CH=C(CH₃)- | -C(=N-OCH₃)- |
| 4-F₃C-C₆H₄- | -CH₂-CH(CH₃)- | -C(=O)- |
| 4-F₃C-C₆H₄- | -CH₂-CH(CH₃)- | -CH(OH)- |
| 4-F₃C-C₆H₄- | -CH₂-CH(CH₃)- | -C(=N-OCH₃)- |
| 4-Cl, 2-F-C₆H₃- | -CH₂-CH(CH₃)- | -CH(O-CH₂-(4-Cl-C₆H₄))- |
| 2,4-Cl₂-C₆H₃- | -CH₂-CH(CH₃)- | -CH(O-CH₂-(2,4-Cl₂-C₆H₃))- |

-continued $$Ar-A-X-CH-N\underset{CH_3}{\overset{}{|}}\diagdown\underset{N}{\overset{N}{\diagup}}\diagdown\underset{}{\overset{}{\diagdown}} \quad (I)$$

| Ar | A | X |
|---|---|---|
| 2,4-dichlorophenyl | −CH₂−CH(CH₃)− | −CH(OCH₂C₆H₅)− |
| 4-chlorophenyl | −CH₂−CH(CH₃)− | 1,3-dioxolan-2-ylidene (C(O−CH₂−CH₂−O)) |
| 4-(F₂CHO)phenyl | −CH=C(CH₃)− | −C(=O)− |
| 4-(F₂CHO)phenyl | −CH=CH− | −C(=O)− |
| 4-(F₂CHO)phenyl | −CH₂−CH₂− | −C(=O)− |
| 4-(F₂CHO)phenyl | −CH₂−CH₂− | −CH(OH)− |
| 4-(F₂CHO)phenyl | −CH₂−CH₂− | −C(=N−OCH₃)− |
| 4-(F₂CHO)phenyl | −CH₂−CH₂− | −CH(O−CH₂−C₆H₄−4-Cl)− |
| 4-(F₂CHO)phenyl | −CH₂−CH(CH₃)− | −C(=O)− |
| 4-(F₂CHO)phenyl | −CH₂−CH(CH₃)− | −CH(OH)− |
| 4-(F₂CHO)phenyl | −CH₂−CH(CH₃)− | −C(=N−OCH₃)− |
| 4-(ClF₂CO)phenyl | −CH=C(CH₃)− | −C(=O)− |

-continued $$Ar-A-X-\underset{CH_3}{\underset{|}{CH}}-N\underset{N=\!\!\!\diagdown}{\overset{\diagup\!\!\!=\!\!N}{\diagdown}} \qquad (I)$$

| Ar | A | X |
|---|---|---|
| ClF₂CO-C₆H₄- | -CH=CH- | -C(=O)- |
| ClF₂CO-C₆H₄- | -CH₂-CH₂- | -C(=O)- |
| ClF₂CO-C₆H₄- | -CH₂-CH₂- | -CH(OH)- |
| ClF₂CO-C₆H₄- | -CH₂-CH₂- | -C(=N-OCH₃)- |
| ClF₂CO-C₆H₄- | -CH₂-CH₂- | -CH(O-CH₂-C₆H₄-4-Cl)- |
| ClF₂CO-C₆H₄- | -CH₂-CH(CH₃)- | -C(=O)- |
| ClF₂CO-C₆H₄- | -CH₂-CH(CH₃)- | -CH(OH)- |
| ClF₂CO-C₆H₄- | -CH₂-CH(CH₃)- | -C(=N-OCH₃)- |
| ClFCHO-C₆H₄- | -CH=C(CH₃)- | -C(=O)- |
| ClFCHO-C₆H₄- | -CH=CH- | -C(=O)- |
| ClFCHO-C₆H₄- | -CH₂-CH₂- | -C(=O)- |
| ClFCHO-C₆H₄- | -CH₂-CH₂- | -CH(OH)- |

-continued

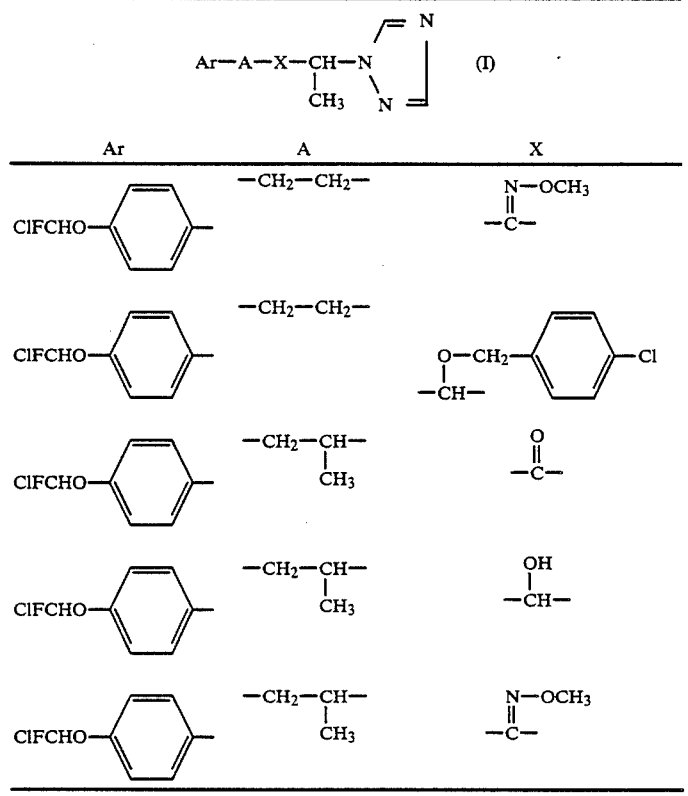

If, for example, 4-chlorobenzaldehyde and 3-(1,2,4-triazol-1-yl)-butan-2-one are used as starting substances, the course of the reaction of process (a) according to the invention may be represented by the following equation:

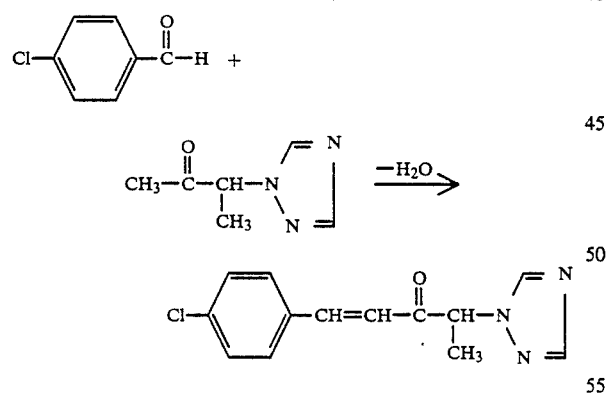

If, for example, 1-(4-chlorophenyl)-4-(1,2,4-triazol-1-yl)-pent-1-en-3-one and hydrogen are used as starting substances and Raney nickel is used as the hydrogenation catalyst, the course of process (b) according to the invention may be represented by the following equation:

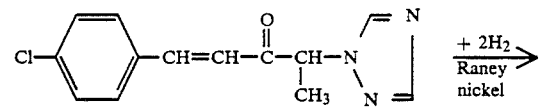

-continued

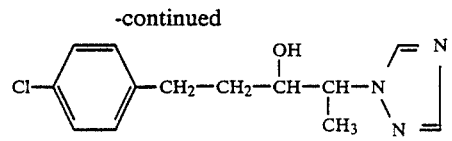

If, for example, 1-(4-chlorophenyl)-4-(1,2,4-triazol-1-yl)-pent-1-en-3-one is used as the starting compound and sodium borohydride is used as the complex hydride, the course of process (c) according to the invention may be represented by the following equation:

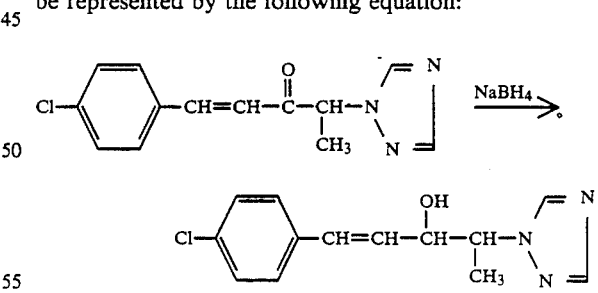

If, for example, 1-(4-chlorophenyl)-4-(1,2,4-triazol-1-yl)-pent-1-en-3-ol and 4-chlorobenzyl chloride are used as the starting substances, the course of process (d) according to the invention may be represented by the following equation:

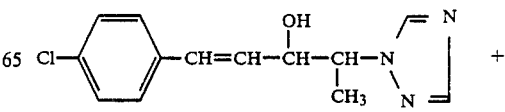

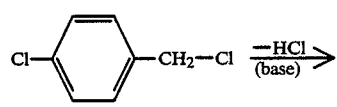

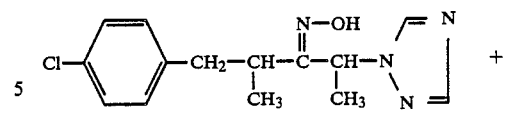

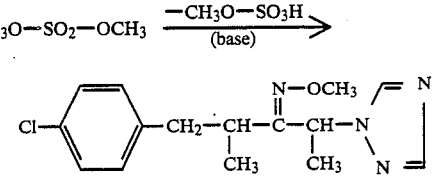

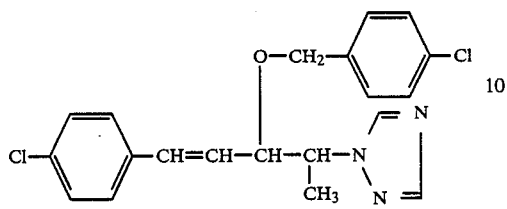

If, for example, 1-(4-chlorophenyl)-4-(1,2,4-triazol-1-yl)-pentan-3-ol is used as the starting compound and dimethyl sulphoxide as the oxidizing agent, the course of process (e) according to the invention may be represented by the following equation:

If, for example, 1-(2,4-dichlorophenyl)-4-(1,2,4-triazol-1-yl)-pentan-3-one and 3-chloropropane-1,2-diol are used as the starting substances, the course of process (h) according to the invention may be represented by the following equation:

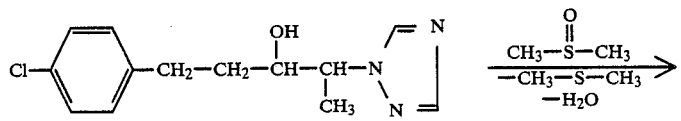

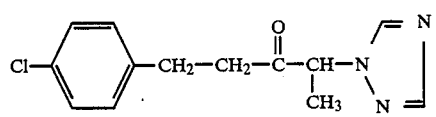

If, for example, 1-(4-chlorophenyl)-4-(1,2,4-triazol-1-yl)-pent-1-en-3-one and 0-(2-chlorobenzyl)hydroxylamine are used as the starting substances, the course of process (f) according to the invention may be represented by the following equation:

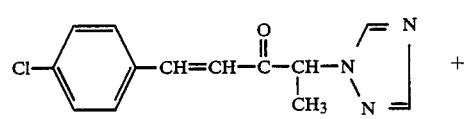

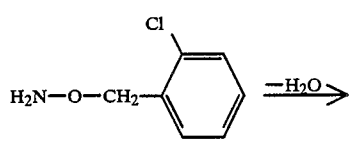

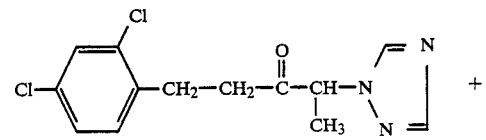

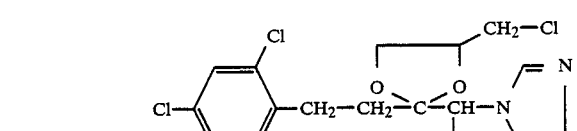

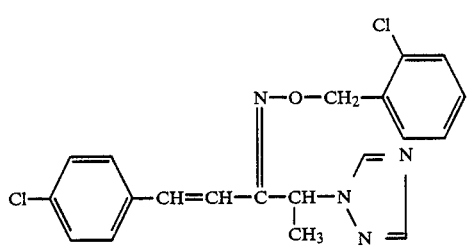

If, for example, 1-(4-chlorophenyl)-2-methyl-4-(1,2,4-triazol-1-yl)-pentan-3-one oxime and dimethyl sulphate are used as the starting substances, the course of process (g) according to the invention may be represented by the following equation:

Formula (II) provides a general definition of the aromatic aldehydes required as starting substances for carrying out process (a) according to the invention. In this formula (II), Ar preferably stands for those radicals which have already been mentioned in connection with the description of the substances of the formula (I) according to the invention as being preferred for this substituent.

The aromatic aldehydes of the formula (II) are generally known compounds of organic chemistry (cf., for example, DE-OS (German Published Specification) No. 3,017,339 and J. Med. Chem. 16, 1399 [1973]).

Formula (III) provides the general definition of the triazolyl ketones furthermore required as starting substances for carrying out process (a) according to the invention. In this formula (III), $R^1$ preferably stands for those radicals which have already been mentioned in connection with the substances of the formula (I) according to the invention as being preferred for this substituent.

The triazolyl ketones of the formula (III) are known (cf. DE-OS (German Published Specification) No. 2,431,407).

Formula (Ia) provides a general definition of the substituted triazoles required as starting substances for carrying out processes (b) and (c) according to the invention. In this formula (Ia), $R^1$ and Ar preferably stand for those radicals which have already been mentioned in connection with the description of the substances of the formula (I) according to the invention as being preferred for these substituents.

The substituted triazoles of the formula (Ia) are compounds according to the invention and may be prepared by process (a) according to the invention.

Formula (Ie) provides a general definition of the substituted triazoles required as starting substances for carrying processes (d) and (e) according to the invention. In this formula (Ie), Ar and A preferably stand for those radicals which have already been mentioned in connection with the description of substances of the formula (I) according to the invention as being preferred for these substituents.

The substituted triazoles of the formula (Ie) are compounds according to the invention and may be prepared by processes (b) or (c) according to the invention.

Formula (IV) provides a general definition of the compounds furthermore required as starting substances for carrying out process (d) according to the invention. In this formula (IV), $R^7$ preferably stands for those radicals which have already been mentioned in connection with the description of the substances of the formula (I) according to the invention as being preferred for the substituent $R^3$, with the exception of the hydrogen radical.

E preferably stands for halogen, in particular for chlorine, bromine or iodine, or for another leaving group which is customary in alkylating or acylating agents, such as, for example, for an alkyl, alkoxy or arylsulphonyloxy radical or an anhydride radical.

E particularly preferably stands for chlorine, bromine, iodine, methylsulphonyloxy, p-methyl-phenylsulphonyloxy or an acetic or propionic anhydride radical.

The compounds of the formula (IV) are generally known compounds of organic chemistry.

Formula (If) provides a general definition of the substituted triazoles required as starting substances for carrying out processes (f) and (h) according to the invention. In this formula (If), Ar and A preferably stand for those radicals which have already been mentioned in connection with the description of the substances of the formula (I) according to the invention as being preferred for these substituents.

The substituted triazoles of the formula (If) are compounds according to the invention and may be prepared by processes (a), (b) or (e) according to the invention.

Formula (V) provides a general definition of the hydroxylamine derivatives furthermore required as starting substances for carrying out process (f) according to the invention. In this formula (V), $R^4$ preferably stands for those radicals which have already been mentioned in connection with the description of the substances of the formula (I) according to the invention as being preferred for these substituents.

The hydroxylamine derivatives of the formula (V) and their acid addition salts, such as, for example, their hydrochlorides or hydroacetates, are generally known compounds of organic chemistry.

Formula (Ii) provides a general definition of the substituted triazoles required as starting substances for carrying out process (g) according to the invention. In this formula (Ii), Ar and A preferably stand for those radicals which have already been mentioned in connection with the description of the substances of the formula (I) according to the invention as being preferred for these substituents.

The substituted triazoles of the formula (Ii) are compounds according to the invention and may be prepared by process (f) according to the invention.

Formula (VI) provides a general definition of the compounds furthermore required as starting substances for carrying out process (g) according to the invention. In this formula (VI), $R^8$ preferably stands for those radicals which have already been mentioned in connection with the description of the substances of the formula (I) as being preferred for the substituent $R^4$, with the exception of the hydrogen radical and the optionally substituted aryl radical.

$E^1$ preferably stands for halogen, in particular for chlorine, bromine or iodine, or for another leaving group customary in alkylating agents, such as, for example, an alkyl, alkoxy or arylsulphonyloxy group.

$E^1$ particularly preferably stands for chlorine, bromine, iodine, methylsulphonyloxy or p-methylphenylsulphonyloxy.

The compounds of the formula (VI) are generally known compounds of organic chemistry.

Formulae (VII), (VIII) and (IX) provide general definitions of the alcohols and diols furthermore required as starting substances for carrying out process (h) according to the invention. In formulae (VII) and (VIII), $R^5$ and $R^6$ each preferably stand for alkyl having 1 to 6 carbon atoms or aralkyl having 6 to 10 carbon atoms in the aryl moiety and 1 to 4 carbon atoms in the straight-chain or branched alkyl moiety, it being possible for each of the aryl radicals to be monosubstituted or polysubstituted by identical or different substituents from the series comprising halogen, cyano, nitro, in each case straight-chain or branched alkyl, alkoxy or alkylthio, each having 1 to 4 carbon atoms, and in each case straight-chain or branched halogenoalkyl, halogenoalkoxy and/or halogenoalkylthio, each having 1 to 4 carbon atoms and 1 to 9 identical or different halogen atoms.

In formula (IX), Y preferably stands for an alkylene radical having 2 to 4 carbon atoms, it being possible for the alkylene radical to be monosubstituted or polysubstituted by identical or different substituents from the series comprising straight-chain or branched alkyl having 1 to 4 carbon atoms, straight-chain or branched halogenoalkyl having 1 to 4 carbon atoms and 1 to 9 identical or different halogen atoms, alkoxyalkyl having 1 to 4 carbon atoms in the alkyl moiety and 1 to 4 carbon atoms in the alkoxy moiety, and/or arylalkyloxyalkyl having 6 to 10 carbon atoms in the aryl moiety and 1 to 4 carbon atoms in the straight-chain or branched alkyloxy moiety and also 1 to 4 carbon atoms in the straight-chain or branched alkyl moiety, it being possible for the aryl moiety to be monosubstituted or polysubstituted by identical or different substituents from the series comprising halogen and/or alkyl having 1 to 4 carbon atoms.

Particularly preferred alcohols of the formula (VII) and (VIII) are those in which $R^5$ or $R^6$ each stand for methyl, ethyl or benzyl, it being possible for the benzyl radical to be monosubstituted, disubstituted or trisubstituted in the phenyl moiety by substituents from the series comprising fluorine, chlorine, bromine, cyano, nitro, methyl, ethyl, n- or i-propyl, n-, i-, s- or t-butyl, methoxy, ethoxy, n- or i-propoxy, methylthio, trifluoromethyl, trifluoromethoxy or trifluoromethylthio.

Other especially preferred diols of the formula (IX) are those in which Y stands for a 1,2-ethanediyl radical which can be monosubstituted to tetrasubstituted by identical or different substituents from the series comprising methyl, ethyl, n- or i-propyl, n-butyl, chloromethyl, trifluoromethyl, methoxymethyl, ethoxymethyl, methoxyethyl, ethoxymethyl and/or benzyloxymethyl which is optionally monosubstituted, disubstituted or trisubstituted in the phenyl moiety by identical or different substituents from the series comprising fluorine, chlorine, bromine, methyl and/or ethyl.

Very particularly preferred alcohols of the formulae (VII) and (VIII) are those in which $R^5$ or $R^6$ each stand for methyl, ethyl or benzyl.

Finally, very particularly preferred diols of the formula (IX) are also those in which Y stands for a 1,2-ethane-diyl radical which is optionally substituted by methyl or chloromethyl.

The alcohols of the formulae (VII) and (VIII) and also the diols of the formula (IX) are generally known compounds of organic chemistry.

Suitable diluents for carrying out process (a) according to the invention are inert organic solvents. Diluents which can preferably be used are aliphatic, alicyclic and aromatic, optionally halogenated hydrocarbons, such as, for example, benzine, benzene, toluene, xylene, chlorobenzene, petroleum ether, hexane, cyclohexane, dichloromethane, chloroform and carbon tetrachloride, ethers, such as diethyl ether, dioxane, tetrahydrofuran or ethylene glycol dimethyl or ethylene glycol diethyl ether, nitriles, such as acetonitrile or propionitrile, amides, such as dimethylformamide, dimethylacetamide, N-methylformanilide, N-methylpyrrolidone or hexamethylphosphoric triamide, sulphoxides, such as dimethyl sulphoxide, alcohols, such as methanol, ethanol or propanol, or heterocyclic bases, such as pyridine, and, if appropriate, also their mixtures with water.

If appropriate, it is also possible for process (a) according to the invention to be carried out in a two-phase system, such as, for example, water/toluene or water/dichloromethane, if appropriate in the presence of a phase transfer catalyst. Examples of such catalysts which may be mentioned are: tetrabutylammonium iodide, tetrabutylammonium bromide, tributyl-methyl-phosphonium bromide, trimethyl-$C_{13}$/$C_{15}$-alkylammonium chloride, dibenzyldimethylammonium methyl-sulphate, dimethyl-$C_{12}$/$C_{14}$-alkylbenzylammonium chloride, tetrabutylammonium hydroxide, 15-crown-5, 18-crown-6, triethylbenzylammonium chloride, trimethylbenzylammonium chloride or tris-[2-(2-methoxyethoxy)-ethyl]-amine.

Process (a) according to the invention is preferably carried out in the presence of a suitable reaction auxiliary. Suitable reaction auxiliaries are all inorganic or organic bases or acids which can customarily be used. The hydroxides, alkoxides, carbonates or hydrogen carbonates of alkali metals, such as, for example, sodium hydroxide, sodium methoxide, sodium ethoxide, potassium t-butoxide, sodium carbonate, potassium carbonate or sodium hydrogen carbonate, and also amines, such as, for example, triethylamine, N,N-dimethylaniline, pyridine, piperidine, N,N-dimethylaminopyridine, diazabicyclooctane (DABCO), diazabicyclononene (DBN) or diazabicycloundecene (DBU), or acids, such as, for example, hydrochloric acid or acetic acid, and also mixtures of acids and bases of the abovementioned type, can preferably be used.

When carrying out process (a) according to the invention, the reaction temperatures can be varied within a relatively wide range. In general, the process is carried out at temperatures of between $-50°$ C. and $+200°$ C., preferably at temperatures of between $0°$ C. and $150°$ C.

1.0 to 1.5 moles, preferably 1.0 to 1.2 moles, of triazolyl ketone of the formula (III) and if appropriate 0.01 to 1.0 mole, preferably 0.1 to 0.5 mole, of reaction auxiliary are generally employed per mole of aromatic aldehyde of the formula (II) for carrying out process (a) according to the invention.

The reaction is carried out, and the reaction products are worked up and isolated by generally customary methods (cf. also the preparation examples).

Suitable hydrogenation catalysts for carrying out process (b) according to the invention are all customary noble metal, noble metal oxide and Raney hydrogenation catalysts. Raney nickel is particularly preferably used as a hydrogenation catalyst.

Suitable diluents for carrying out process (b) according to the invention are also inert organic solvents. The diluents mentioned in process (a) or esters, such as ethyl acetate, are preferably used.

When carrying out process (b) according to the invention, the reaction temperatures can be varied within a relatively wide range. In general, the process is carried out at temperatures of between $0°$ C. and $200°$ C., preferably at temperatures of between $20°$ C. and $150°$ C.

Process (b) according to the invention is generally carried out under pressure. The process is preferably carried out under a hydrogen pressure of between 1 and 200 bar, in particular between 10 and 100 bar.

0.001 to 0.5 mole, preferably 0.01 to 0.1 mole, of hydrogenation catalyst and also an excess of hydrogen are generally employed per mole of substituted triazole of the formula (Ia) for carrying out process (b) according to the invention.

The reaction is carried out, and the reaction products are worked up and isolated by generally customary methods.

Depending on the types of the substituents in the starting compounds of the formula (Ia) and depending on the reaction conditions (temperature, amount of catalyst, hydrogen pressure, reaction time) the initial result is hydrogenation of the C=C double bond in the molecule and then possibly further hydrogenation of the C=O double bond, so that either 1-aryl-4-triazolylpentan-3-ones or 1-aryl-4-triazolylpentan-3-ols can be obtained as the final products (cf. also the preparation examples).

Process (c) according to the invention is carried out in the presence of a customary complex hydride as the reducing agent. Sodium borohydride, sodium cyanoborohydride or lithium borohydride are particularly preferably used, if appropriate in the presence of calcium chloride, it also being possible for complex calcium borohydrides to be formed in the reaction mixture.

Suitable diluents for carrying out process (c) according to the invention are inert organic solvents. Ethers, such as diethyl ether, dioxane, tetrahydrofuran or ethylene glycol dimethyl or ethylene glycol diethyl ether, or alcohols, such as methanol, ethanol and also n- or i-propanol, are preferably used, if appropriate also in the form of a mixture with water.

When carrying out process (c) according to the invention, the reaction temperatures can be varied within a relatively wide range. In general, the process is carried out at temperatures of between $-100°$ C. and $+200°$ C., preferably at temperatures of between $-50°$ C. and $+50°$ C.

0.1 to 1.5 moles, preferably 0.25 to 1.0 mole, of complex hydride and if appropriate 0.1 to 1.5 moles, preferably 0.25 to 1.0 mole, of calcium chloride are generally employed per mole of substituted triazole of the formula (Ia) for carrying out process (c) according to the invention.

The reaction is carried out, and the reaction products are worked up and isolated by generally customary methods (cf. also the preparation examples).

Suitable diluents for carrying out process (d) according to the invention are inert organic solvents. Aliphatic, alicyclic or aromatic optionally halogenated hydrocarbons, such as, for example, benzine, benzene, toluene, xylene, chlorobenzene, petroleum ether, hexane, cyclohexane, dichloromethane, chloroform and carbon tetrachloride, ethers, such as diethyl ether, dioxane, tetrahydrofuran or ethylene glycol dimethyl or ethylene glycol diethyl ether, ketones, such as acetone or butanone, nitriles, such as acetonitrile or propionitrile, amides, such as dimethylformamide, dimethylacetamide, N-methylformanilide, N-methylpyrrolidone or hexamethylphosphoric triamide, esters, such as ethyl acetate, or sulphoxides, such as dimethyl sulphoxide, can preferably be used.

If appropriate, process (d) according to the invention can alternatively be carried out in a two-phase system, such as, for example, water/toluene or water/dichloromethane, if appropriate in the presence of a phase transfer catalyst. Examples of such catalysts which may be mentioned are: tetrabutylammonium iodide, tetrabutylammonium bromide, tributyl-methylphosphonium bromide, trimethyl-$C_{13}$/$C_{15}$-alkylammonium chloride, dibenzyldimethylammonium methylsulphate, dimethyl-$C_{12}$/$C_{14}$-alkyl-benzylammonium chloride, tetrabutylammonium hydroxide, 15-crown-5, 18-crown-6, triethylbenzylammonium chloride and trimethylbenzylammonium chloride.

Process (d) according to the invention is preferably carried out in the presence of a suitable reaction auxiliary. Suitable reaction auxiliaries are all inorganic or organic bases which can customarily be used. The hydrides, hydroxides, amides, alkoxides, carbonates or hydrogen carbonates of alkali metals, such as, for example sodium hydride, sodium amide, sodium hydroxide, sodium methoxide, sodium ethoxide, potassium t-butoxide, sodium carbonate or sodium hydrogen carbonate, and also tertiary amines, such as triethylamine, N,N-dimethylaniline, pyridine, N,N-dimethylaminopyridine, diazabicyclooctane (DABCO), diazabicyclononene (DBN) or diazabicycloundecene (DBU) are preferably used.

When carrying out the reactions of process (d) according to the invention, it can also be advantageous to add small amounts of customary alkylation catalysts, such as, for example, potassium iodide.

When carrying out process (d) according to the invention, the reaction temperatures can be varied within a relatively wide range. In general, the process is carried out at temperatures of between $-50°$ C. and $200°$ C., preferably at temperatures of between $0°$ C. and $100°$ C.

1.0 to 5.0 moles, preferably 1.0 to 1.5 moles, of a compound of the formula (IV) and if appropriate 1.0 to 3.0 moles, preferably 1.0 to 1.2 moles, of reaction auxiliary are generally employed per mole of substituted triazole of the formula (Ie) for carrying out process (d) according to the invention.

The reaction is carried out, and the reaction products are worked up and isolated by generally customary methods (cf. also the preparation examples).

Suitable oxidizing agents for carrying out process (e) according to the invention are all oxidizing agents which are customarily used in oxidation reactions of alcohols of this type. Dimethyl sulphoxide in the presence of suitable auxiliary reagents, such as, for example, oxalyl chloride in the presence of triethylamine or acetic anhydride, or sulphur trioxide in the presence of pyridine and triethylamine, or p-toluenesulphonyl chloride or sulphonic anhydrides, such as methanesulphonic anhydride or trifluoromethanesulphonic anhydride, or cyanuric halides or chlorine or mercury acetate or silver tetrafluoroborate in the presence of triethylamine, or potassium iodide in the presence of sodium hydrogen carbonate, which bind the water liberated during the reaction, are particularly preferably used.

Suitable diluents for carrying out process (e) according to the invention are inert organic solvents. Aliphatic, alicyclic or aromatic optionally halogenated hydrocarbons, such as, for example, benzine, benzene, toluene, xylene, chlorobenzene, petroleum ether, hexane, cyclohexane, dichloromethane, chloroform and carbon tetrachloride, ethers, such as diethyl ether, dioxane, tetrahydrofuran or ethylene glycol dimethyl or ethylene glycol diethyl ether, ketones, such as acetone or butanone, nitriles, such as acetonitrile or propionitrile, amides, such as dimethylformamide, dimethylacetamide, N-methylformanilide, N-methylpyrrolidone or hexamethylphosphoric triamide, esters, such as ethyl acetate, or sulphoxides, such as dimethyl sulphoxide, which can be employed simultaneously as the oxidizing agent and as the diluent, can preferably be used.

When carrying out process (e) according to the invention, the reaction temperatures can be varied within a relatively wide range. In general, the process is carried out at temperatures of between $-80°$ C. and $+50°$ C., preferably at temperatures of between $-80°$ C. and $0°$ C.

1.0 to 30.0 moles, preferably 1.0 to 5.0 moles, of oxidizing agent are employed per mole of substituted triazole of the formula (Ie) for carrying out process (e) according to the invention.

The reaction is carried out, and the reaction products are worked up and isolated by generally customary methods (cf. also the preparation examples).

Suitable diluents for carrying out process (f) according to the invention are inert organic solvents. Aliphatic, alicyclic or aromatic, optionally halogenated hydrocarbons, such as, for example, benzine, benzene, toluene, xylene, chlorobenzene, petroleum ether, hexane, cyclohexane, dichloromethane, chloroform and carbon tetrachloride, ethers, such as diethyl ether, dioxane, tetrahydrofuran or ethylene glycol dimethyl or ethylene glycol diethyl ether, nitriles, such as acetonitrile or propionitrile, amides, such as dimethylformamide, dimethylacetamide, N-methylformanilide, N-methylpyrrolidone or hexamethylphosphoric triamide, esters, such as ethyl acetate, or sulphoxides, such as dimethyl sulphoxide, alcohols, such as methanol or ethanol, or basic solvents, such as pyridine of triethylamine, can preferably be used.

Process (f) according to the invention is preferably carried out in the presence of a suitable reaction auxiliary. Suitable reaction auxiliaries are all inorganic and organic bases which can customarily be employed. The hydrides, hydroxides, alkoxides, carbonates or hydrogen carbonates of alkali metals, such as, for example, sodium hydroxide, sodium methoxide, sodium ethoxide, potassium t-butoxide, sodium carbonate, potassium carbonate or sodium hydrogen carbonate, and also tertiary amines, such as, for example, triethylamine, N,N-dimethylaniline, pyridine, N,N-dimethylaminopyridine, diazabicyclooctane (DABCO), diazabicyclononene (DBN) or diazabicycloundecene (DBU) are preferably used. If appropriate, acid reaction auxiliaries such as, for example, p-toluenesulphonic acid, are also advantageous.

When carrying out process (f) according to the invention, the reaction temperatures can be varied within a relatively wide range. In general, the process is carried out at temperatures of between −50° C. and +150° C., preferably at temperatures of between 0° C. and 50° C.

1.0 to 2.0 moles, preferably 1.0 to 1.2 moles, of hydroxylamine derivative of the formula (V) or of a corresponding acid addition salt, and if appropriate 0.01 to 20.0 moles, preferably 0.1 to 3.0 moles, of reaction auxiliary are employed per mole of substituted triazole of the formula (If) for carrying out process (f) according to the invention.

The reaction is carried out, and the reaction products are worked up and isolated by generally customary methods (cf. also the preparation examples).

Suitable diluents for carrying out process (g) according to the invention are inert organic solvents. Aliphatic, alicyclic or aromatic, optionally halogenated hydrocarbons, such as, for example, benzine, benzene, toluene, xylene, chlorobenzene, petroleum ether, hexane, cyclohexane, dichloromethane, chloroform and carbon tetrachloride, ethers, such as diethyl ether, dioxane, tetrahydrofuran or ethylene glycol dimethyl or ethylene glycol diethyl ether, ketones, such as acetone or butanone, nitriles, such as acetonitrile or propionitrile, amides, such as dimethylformamide, dimethylacetamide, N-methylformanilide, N-methylpyrrolidone or hexamethylphosphoric triamide, esters, such as ethyl acetate, or sulphoxides, such as dimethyl sulphoxides, can preferably be used.

If appropriate, process (g) can alternatively be carried out in a two-phase system, such as, for example, water/toluene or water/dichloromethane, if appropriate in the presence of a phase transfer catalyst. Examples of such catalysts which may be mentioned are: tetrabutylammonium iodide, tetrabutylammonium bromide, tributylmethylphosphonium bromide, trimethyl-$C_{13}$/$C_{15}$-alkylammmonium chloride, dibenzyl-dimethylammonium methylsulphate, dimethyl-$C_{12}$/$C_{14}$-alkyl-benzylammonium chloride, tetrabutylammonium hydroxide, 15-crown-5, 18-crown-6, triethylbenzylammonium chloride and trimethylbenzylammonium chloride.

Process (g) according to the invention is preferably carried out in the presence of a suitable reaction auxiliary. Suitable reaction auxiliaries are all the inorganic and organic bases which can customarily be used. The hydrides, hydroxides, alkoxides, carbonates or hydrogen carbonates of alkali metals, such as, for example, sodium hydride, sodium hydroxide, sodium methoxide, sodium ethoxide, potassium t-butoxide, sodium carbonate, potassium carbonate or sodium hydrogen carbonate, and also tertiary amines, such as, for example, triethylamine, N,N-dimethylaniline, pyridine, N,N-dimethylaminopyridine, diazabicyclooctane (DABCO), diazabicyclononene (DBN) or diazabicycloundecene (DBU) are preferably used.

When carrying out process (g) according to the invention, the reaction temperatures can be varied within a relatively wide range. In general, the process is carried out at temperatures of between 0° C. and 120° C., preferably at temperatures of between 20° C. and 100° C.

1.0 to 10.0 moles, preferably 1.0 to 3.0 moles, of a compound of the formula (VI) and if appropriate 1.0 to 5.0 moles, preferably 1.0 to 3.0 moles, of reaction auxiliary are generally employed per mole of substituted triazole of the formula (Ii) for carrying out process (g) according to the invention.

The reaction is carried out, and the reaction products are worked up and isolated by generally customary methods.

Suitable diluents for carrying out process (h) according to the invention are inert organic solvents. Aliphatic, alicyclic or aromatic, optionally halogenated hydrocarbons, such as, for example, benzine, benzene, toluene, xylene, chlorobenzene, petroleum ether, hexane, cyclohexane, dichloromethane, chloroform and carbon tetrachloride, or ethers, such as diethyl ether, dioxane, tetrahydrofuran or ethylene glycol dimethyl or ethylene glycol diethyl ether, can preferably be used.

Process (h) is preferably carried out in the presence of a suitable reaction auxiliary. Suitable reaction auxiliaries are all inorganic or organic acids which can customarily be used, or other customary catalysts. Diluted aqueous or concentrated mineral acids, such as hydrochloric acid, sulphuric acid or phosphoric acid, or organic sulphonic acids, such as methanesulphonic acid or p-toluenesulphonic acid, are particularly preferably used.

When carrying out process (h) according to the invention, the reaction temperatures can be varied within a relatively wide range. In general, the process is carried out at temperatures from between 0° C. and 200° C., preferably at temperatures of between 20° C. and 150° C.

1.0 to 30.0 moles, preferably 1.0 to 5.0 moles, of alcohol or diol of the formulae (VII), (VIII) or (IX), and if appropriate 0.01 to 2.0 moles, preferably 0.1 to 1.0 mole, of reaction auxiliary are employed per mole of substituted triazole of the formula (If) for carrying out process (h) according to the invention.

The reaction is carried out, and the reaction products are worked up and isolated by generally customary methods (cf. also the preparation examples).

The acid addition salts of the compounds of the formula (I) can be prepared in a simple manner by customary salt formation methods, such as, for example, by dissolving a compound of the formula (I) in a suitable inert solvent and adding the acid, such as, for example, hydrochloric acid, and they can be isolated in a known manner, for example by filtration, and, if appropriate, purified by washing with an inert organic solvent.

The metal salt complexes of compounds of the formula (I) can be obtained in a simple manner by customary processes, thus, for example, by dissolving the metal salt in alcohol, for example ethanol, and adding the solution to the compound of the formula (I). Metal salt complexes can be isolated in a known manner, for example by filtration, and, if appropriate, purified by recrystallization.

The active compounds according to the invention exhibit a powerful microbicidal action and can be employed in practice as fungicides and bactericides for combating undesired microorganisms.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal diseases which come under the generic names listed above may be mentioned as examples, but not by way of limitation: Pythium species, such as, for example, *Pythium ultimum;* Phytophthora species, such as, for example, *Phytophthora infestans;* Pseudoperonospora species, such as, for example, *Pseudoperonspora-humuli* or *Pseudoperonospora cubensis;* Plasmopara species, such as, for example, *Plasmopara viticola;* Peronospora species, such as, for example, *Peronospora pisi* or *P. brassicae;* Erysiphe species, such as, for example, *Erysiphe graminis;* Sphaerotheca species, such as, for example, *Erysiphe graminis;* Sphaerotheca species, such as for example, *Sphaerotheca fuliginea;* Podosphaera species, such as, for example, *Podosphaera leucotricha;* Venturia species, such as, for example, *Venturia inaequalis;* Pyrenophora species, such as, for example, *Pyrenophora teres* or *P. graminea* (conidia form: Drechslera, syn: Helminthosporium); Cochliobolus species, such as, for example, *Cochliobolus sativus* (conidia form: Drechslera, syn: Helminthosporium); Uromyces species, such as, for example, *Uromyces appendiculatus;* Puccinia species, such as, for example, *Puccinia recondita;* Tilletia species, such as, for example, *Tilletia caries;* Ustilago species, such as, for example, *Ustilago nuda* or *Ustilago avenae;* Pellicularia species, such as, for example, *Pellicularia sasakii;* Pyricularia species, such as, for example, *Pyriculria oryzae;* Fusarium species, such as, for example, *Fusarium culmorum;* Potrytis species, such as, for example, *Botrytis cinerea;* Septoria species, such as, for example, *Septoria nodorum;* Leptosphaeria species, such as, for example, *Leptosphaeria nodorum;* Cercospora species, such as, for example, *Cercospora canescens;* Alternaria species, such as, for example, *Alternaria brassicae* and Pseudocercosporella species, such as, for example, *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

Here, the active compounds according to the invention can be employed with particularly good success for combating cereal diseases, such as, for example, against the causative organism of leaf spot of wheat (*Leptosphaeria nodorum*) or against the causative organism of net blotch of barley (*Pyrenophora teres*) or against the causative organism of foot rot disease of wheat (*Cochliobolus sativus*) or against the causative organism of powdery mildew of cereals (*Erysiphe graminis*) or against the causative organism of snow mould of cereals (*Fusarium nivale*) or against the causative organism of column rot of cereals (*Fusarium culmorum*), and also for combating diseases in fruit growing and vegetable growing, such as, for example, against the causative organism of apple scab (*Venturia inaequalis*) or against the causative organism of powdery mildew of cucurbits (*Sphaerotheca fuliginea*), or for combating rice diseases, such as, for example, against the causative organism of rice blot disease (*Pyricularia oryzae*).

In addition, the active compounds according to the invention also possess a plant growth-regulating activity.

Finally, the active compounds according to the invention can be employed in the protection of materials for protecting industrial materials against contamination by microorganisms. Technical materials in this context are taken to mean non-living materials which have been prepared for use in industry. For example, industrial materials which are to be protected against change or destruction by microorganisms, are glues, sizes, paper, board, textiles, leather, wood, paints, articles made of plastic, cooling lubricants and other materials which can be contaminated or destroyed by microorganisms. Within the scope of the materials to be protected, parts of production plants which can be impaired by multiplication of microorganisms, may also be mentioned, for example cooling water circuits. Industrial materials which may be mentioned in the scope of the present invention preferably are glues, sizes, paper and board, leather, wood, paints, cooling lubricants and cooling circuits, wood being particularly preferred.

Microorganisms which can cause a degradation or a change in the industrial materials which may be mentioned are, for example, bacteria, fungi, yeasts, algae and slime organisms. The active substances according to the invention preferably act against fungi, in particular moulds, fungi which discolour and destroy wood (*Basidiomycetes*), and against slime organisms and algae.

Examples of microorganisms of the genera below which may be mentioned are:
Alternaria, such as *Alternaria tenuis,*
Aspergillus, such as *Aspergillus niger,*
Chaetomium, such as *Chaetomium globosum,*
Coniophora, such as *Coniophora puteana,*
Lentinus, such as *Lentinus tigrinus,*
Penicillium, such as *Penicillium glaucum,*
Polyporus, such as *Polyporus versicolor,*
Aureobasidium, such as *Aureobasidium pullulans,*
Sclerophoma, such as *Sclerophoma pityophila,*
Trichoderma, such as *Trichoderma viride,*
Escherichia, such as *Escherichia coli,*
Pseudomonas, such as *Pseudomonas aeruginosa,*
Staphylococcus, such as *Staphylococcus aureus.*

Depending on their particular physical and/or chemical properties, the active compounds can be converted to the customary formulations, such as solutions, emulsions, suspensions, powders, foams, pastes, granules, aerosols, very fine capsules in polymeric substances and in coating compositions for seed, and also as ULV cold mist and warm mist formulations.

These formulations are produced in a known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main:

aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in the formulations as a mixture with other known active compounds, such as fungicides, insecticides, acaricides and herbicides, as well as in mixtures with fertilizers and growth regulators.

The active compounds can be used as such or in the form of their formulations or the use forms prepared therefrom, such as ready-to-use solutions, suspensions, wettable powders, pastes, soluble powders, dusting agents and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seeds of the plants can also be treated.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

The examples below illustrate the preparation and the use of the active compounds according to the invention.

PREPARATION EXAMPLES

EXAMPLE 1

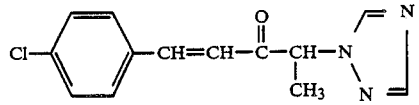

3.8 ml (0.044 mol) of piperidine and 9.8 ml (0.171 mol) of acetic acid are added to 123.4 g (0.878 mol) of 4-chlorobenzaldehyde and 122.6 g (0.881 mol) of 3-(1,2,4-triazol-1-yl)-butan-2-one in 430 ml of chloroform, and the mixture is refluxed over a water separator for 26 hours. For working up, the cooled reaction mixture is washed in succession with 500 ml of water, 200 ml of 40 per cent strength aqueous sodium hydrogen sulphite solution and again with 500 ml of water. The organic phase is dried over sodium sulphate and evaporated under reduced pressure, the residue is taken up in 200 ml of hot ethyl acetate, and the desired product is precipitated by adding 400 ml of petroleum ether.

Following filtering off with suction and drying, 117 g (51% of theory) of 1-(4-chlorophenyl)-4-(1,2,4-triazol-1-yl)-pent-1-en-3-one of melting point 115° C.–116° C. are obtained.

EXAMPLE 2

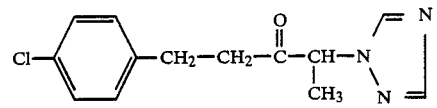

5 g of Raney nickel are added to a solution of 35 g (0.14 mol) of 1-(4-chlorophenyl)-4-(1,2,4-triazol1-yl)-pent-1-en-3-one in 180 ml of methanol, and the mixture is then hydrogenated at 60° C. to 70° C. and a hydrogen pressure of 90 to 100 bar for 2 hours, with stirring. For working up, the reaction mixture is filtered, the filtrate is evaporated, and the residue is recrystallized twice from diisopropyl ether.

24.9 g (71% of theory) of 1-(4-chlorophenyl)-4-(1,2,4-triazol-1-yl)-pentan-3-one of melting point 77° C.–78° C. are obtained.

EXAMPLE 3

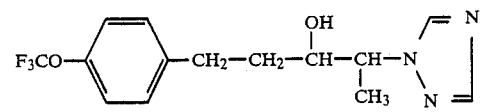

40 g of Raney nickel are added to a solution of 250 g (0.8 mol) of 1-(4-trifluoromethoxyphenyl)-4-(1,2,4-triazol-1-yl)-pent-1-en-3-one in 1,500 ml of methanol, and the mixture is then hydrogenated at 90° C. to 110°

C. and a hydrogen pressure of 90 to 100 bar for 6.5 hours, with stirring. For working up, the reaction mixture is filtered, the filtrate is evaporated, and the residue is crystallized by stirring with diisopropyl ether.

148 g (59% of theory) of 1-(4-trifluoromethoxyphenyl)-4-(1,2,4-triazol-1-yl)-pentan-3-ol of melting point 69° C. are obtained.

EXAMPLE 4

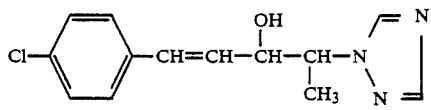

A solution of 1.26 g (0.0333 mol) of sodium borohydride in 15 ml of water is added dropwise, at −5° C. to 0° C., in the course of 30 minutes and with stirring to a suspension of 12.4 g (0.0474 mol) of 1-(4-chlorophenyl)-4-(1,2,4-triazol-1-yl)-pent-1-en-3-one and 3.53 g (0.0318 mol) of anhydrous calcium chloride in 100 ml of isopropanol, and, when the addition is complete, the mixture is stirred at room temperature for 2 hours. For working up, the reaction mixture is evaporated under reduced pressure and the residue remaining is added to a mixture of 150 ml of water and 10 ml of acetic acid. The mixture is extracted several times, using 50-ml portions of dichloromethane. The combined organic phases are washed with water, dried over sodium sulphate and evaporated under reduced pressure, and the residue is recrystallized from 30 ml of acetonitrile.

8.9 g (72% of theory) of 1-(4-chlorophenyl)-4(1,2,4-triazol-1-yl)-pent-1-en-3-ol of melting point 117° C.–118° C. are obtained.

EXAMPLE 5

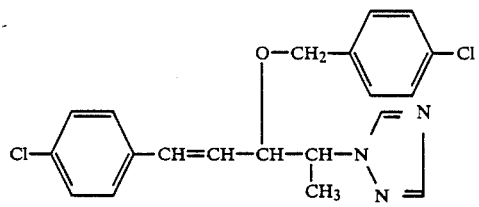

0.2 g (0.0012 mol) of potassium iodide is added to a suspension of 0.36 g (0.012 mol) of 80 percent strength sodium hydride (in paraffin) in 20 ml of absolute dimethoxyethane, and a solution of 2.6 g (0.010 mol) of 1-(4-chlorophenyl)-4-(1,2,4-triazol-1-yl)-pent-1-en-3-ol in 10 ml of dimethoxyethane is then added dropwise, at 0° C. and with stirring. When the evolution of gas has ceased, 1.6 g (0.010 mol) of 4-chlorobenzyl chloride in 5 ml of dimethoxyethane are then added, and the mixture is stirred for 4 hours at room temperature and then for 20 hours at 40° C. 10 ml of isopropanol are added to the cooled reaction mixture, the mixture is then poured into ice water and extracted three times with dichloromethane, the organic phase is dried over sodium sulphate and concentrated under reduced pressure, and the residue is crystallized by treatment with a mixture of diethyl ether/n-hexane/ethanol=(5:3:1).

0.6 g (16% of theory) of 1-(4-chlorophenyl)-3-(4-chlorobenzyloxy)-4-(1,2,4-triazol-1-yl)-pent-1-ene of melting point 91° C. are obtained.

EXAMPLE 6

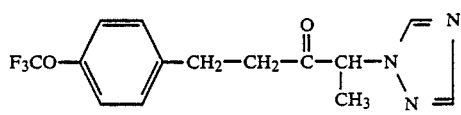

9.4 g (0.12 mol) of dimethyl sulphoxide in 10 ml of dichloromethane are added dropwise, at −50° C. and in the course of 10 minutes to a solution of 7.0 g (0.055 mol) of oxalyl chloride in 25 ml of absolute dichloromethane. A suspension of 15.8 g (0.05 mol) of 1-(4-trifluoromethoxyphenyl)-4-(1,2,4-triazol-1-yl)-pentan-3-ol in 25 ml of dichloromethane is then added to the mixture, likewise at −50° C., the mixture is stirred at −50° C. for 20 minutes, 25.3 g (0.25 mol) of triethylamine are then added, and the mixture is stirred at −50° C. for a further 10 minutes. For working up, the temperature of the reaction mixture is allowed to rise to 0° C., 20 ml of water are added, and the organic phase is separated off. The organic phase is dried over magnesium sulphate, and the solvent is removed under reduced pressure (0.05 mbar/50° C. ).

15 g (96% of theory) of 1-(4-trifluoromethoxyphenyl)-4-(1,2,4-triazol-1-yl)-pentan-3-one of melting point 58° C. are obtained.

EXAMPLE 7

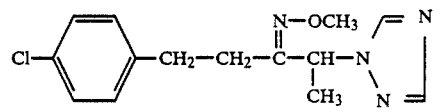

3.17 g (0.0379 mol) of 0-methylhydroxylamine hydrochloride are added to 10.0 g (0.0379 mol) of 1-(4-chlorophenyl)-4-(1,2,4-triazol-1-yl)-pentan-3-one in 75 ml of dry pyridine. The reaction mixture is stirred for 20 hours at room temperature and then evaporated under reduced pressure, the residue is taken up in dichloromethane and washed with water, the organic phase is dried over sodium sulphate and evaporated, again under reduced pressure, and the residue is chromatographed on silica gel (eluent: ethyl acetate).

7.2 g (65% of theory) of 1-(4-chlorophenyl)-3-methoximino-4-(1,2,4-triazol-1-yl)-pentane are obtained as an oil of refractive index $n_D^{20}$ 1.5448.

EXAMPLE 8

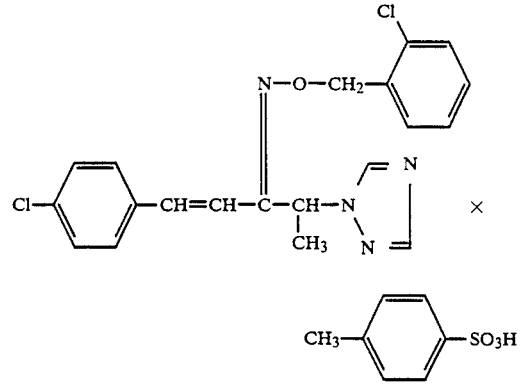

3.2 g (0.02 mol) of 0-(2-chlorobenzyl)-hydroxylamine and 5.2 g (0.02 mol) of 1-(4-chlorophenyl)-4-(1,2,4- triazol-1-yl)-pent-1-en-3-one are refluxed for 18 hours over a water separator, together with 2.0 g (0.012 mol) of p-toluenesulphonic acid in 160 ml of toluene. The salt which has precipitated in the cooled reaction mixture is filtered off and briefly stirred with saturated aqueous sodium hydrogen carbonate solution, the mixture is filtered, and the residue is triturated with diethyl ether.

5.7 g (50% of theory) of 1-(4-chlorophenyl)-3(2-chlorobenzyloximino)-4-(1,2,4-triazol-1-yl)-pent-1-ene p-toluenesulphonate of melting point 167° C. are obtained.

EXAMPLE 9

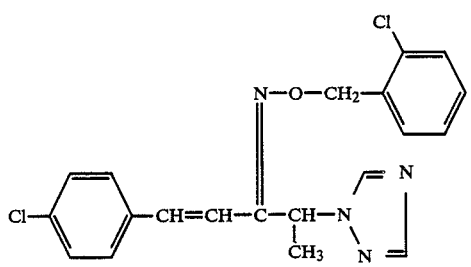

5.5 g (0.0096 mol) of 1-(4-chlorophenyl)-3-(2-chlorobenzyloximino)-4-(1,2,4-triazol-1-yl)-pent-1-ene p-toluenesulphonate are stirred together with 2.0 g (0.02 mol) of triethylamine in 20 ml of dichloromethane at room temperature for 10 minutes. The reaction mixture is then washed with 10 ml of water, the organic phase is dried over sodium sulphate, and the solvent is removed under reduced pressure.

3.6 g (99% of theory) of 1-(4-chlorophenyl)-3-(2-chlorobenzyloximino)-4-(1,2,4-triazol-1-yl)-pent-1-ene are obtained as an oil of refractive index $n_D^{20}$ 1.6101.

EXAMPLE 10

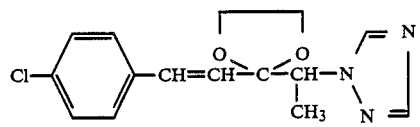

3.5 g (0.013 mol) of 1-(4-chlorophenyl)-4-(1,2,4-triazol-1-yl)-pent-1-en-3-one and 1.77 g (0.016 mol) of 3-chloropropane-1,2-diol are refluxed for 82 hours with 0.1 ml of methanesulphonic acid in 100 ml of absolute toluene. The reaction mixture is then washed 3 times with 100 ml portions of 0.1 N aqueous sodium hydroxide solution and then 3 times with 50 ml portions of water. The organic phase is dried over potassium carbonate, the solvent is distilled off, and the residue is chromatographed graphed over silica gel (eluent: ethyl acetate).

1.45 g (31% of theory) of 2-[1-(1,2,4-triazol-1-yl)-ethyl]-2-[2-(4-chlorophenyl)-ethenyl]-4-chloromethyl1,3-dioxolane are obtained as an oil of refractive index $n_D^{20} = 1.5591$.

The substituted triazoles of the formula

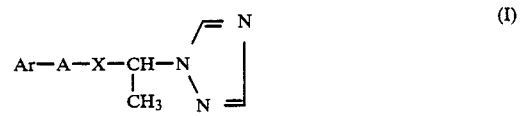 (I)

which are listed in Table 1 below are prepared in an analogous manner and following the general instructions for the preparation.

TABLE 1

| Example No. | Ar | A | X | Physical properties |
|---|---|---|---|---|
| 11 | F₃CO—⟨phenyl⟩— | —CH=CH— | $-\overset{O}{\underset{\|}{C}}-$ | Mp 80–82° C. |
| 12 | 2,4-Cl₂—⟨phenyl⟩— | —CH=CH— | $-\overset{O}{\underset{\|}{C}}-$ | Mp 104–106° C. |
| 13 | F₃CO—⟨phenyl⟩— | —CH=CH— | $-\underset{\|}{C}H-$ OH | $n_D^{20}$ 1.5159 |
| 14 | 2,4-Cl₂—⟨phenyl⟩— | —CH=CH— | $-\underset{\|}{C}H-$ OH | Mp 124–126° C. |
| 15 | F₃CO—⟨phenyl⟩— | —CH=C(CH₃)— | $-\overset{O}{\underset{\|}{C}}-$ | $n_D^{20}$ 1.5310 |

TABLE 1-continued

| Example No. | Ar | A | X | Physical properties |
|---|---|---|---|---|
| 16 | 4-Cl-C6H4- | -CH=C(CH3)- | -C(=O)- | Mp 56–58° C. |
| 17 | 2,4-Cl2-C6H3- | -CH=C(CH3)- | -C(=O)- | Mp 114–116° C. |
| 18 | 4-Cl-C6H4- | -CH=CH- | -C(=N-OCH3)- | Mp 102–104° C. |
| 19 | 4-F3CO-C6H4- | -CH=C(CH3)- | -C(=N-OCH3)- | $n_D^{20}$ 1.5068 |
| 20 | 4-Cl-C6H4- | -CH=C(CH3)- | -C(=N-OCH3)- | $n_D^{20}$ 1.5770 |
| 21 | 4-F3CO-C6H4- | -CH=CH- | -C(=N-OCH3)- | $n_D^{20}$ 1.5400 |
| 22 | 2-Cl-C6H4- | -CH=CH- | -C(=N-OCH3)- | $n_D^{20}$ 1.5408 |
| 23 | 2-Cl-C6H4- | -CH=CH- | 1,3-dioxolan-2-yl with CH2Cl | $n_D^{20}$ 1.5543 |
| 24 | 2,4-Cl2-C6H3- | -CH=C(CH3)- | -C(=N-OCH3)- | $n_D^{20}$ 1.5766 |
| 25 | 2-Cl-C6H4- | -CH=C(CH3)- | -C(=O)- | Mp 78–80° C. |
| 26 | 2,4-Cl2-C6H3- | -CH2-CH2- | -C(=O)- | $n_D^{20}$ 1.5546 |
| 27 | 2,4-Cl2-C6H3- | -CH=CH- | 1,3-dioxolan-2-yl with CH2Cl | $n_D^{20}$ 1.5515 |

TABLE 1-continued

| Example No. | Ar | A | X | Physical properties |
|---|---|---|---|---|
| 28 | 2,4-dichlorophenyl | —CH=CH— | —C(=N—OCH₃)— | $n_D^{20}$ 1.6095 |
| 29 | 2,4-dichlorophenyl | —CH₂—CH₂— | —C(=N—OCH₃)— | $n_D^{20}$ 1.5520 |
| 30 | 2-chlorophenyl | —CH=C(CH₃)— | —C(=N—OCH₃)— | $n_D^{20}$ 1.5720 |
| 31 | 4-chlorophenyl | —CH=CH— | —C(=N—OH)— | Mp 169–170° C. |
| 32 | 4-(F₃CO)phenyl | —CH₂—CH₂— | —C(=N—OCH₃)— | $n_D^{20}$ 1.4918 |
| 33 | 4-(F₃CO)phenyl | —CH=CH— | cyclic carbonate —O—C(=O)—O— with CH₂Cl | $n_D^{20}$ 1.5180 |
| 34 | 4-chlorophenyl | —CH=CH— | —C(=N—O—CH₂—(4-Cl-C₆H₄))— | Mp 96° C. |
| 35 | 4-chlorophenyl | —CH=CH— | —C(=N—O—CH₂—(2,6-Cl₂-C₆H₃))— | $n_D^{20}$ 1.5180 |
| 36 | 4-chlorophenyl | —CH=CH— | —C(=N—O—CH₂—CH₂—C₆H₅)— | Mp 144° C. |
| 37 | 2-chlorophenyl | —CH=CH— | —C(=O)— | $n_D^{20}$ 1.5810 |
| 38 | 4-chlorophenyl | —CH=C(CH₃)— | cyclic carbonate —O—C(=O)—O— with CH₂Cl | $n_D^{20}$ 1.5522 |

TABLE 1-continued

| Example No. | Ar | A | X | Physical properties |
|---|---|---|---|---|
| 39 | 2,4-Cl$_2$-C$_6$H$_3$- | -CH$_2$-CH$_2$- | -CH(CH$_2$Cl)-O-C(=O)-O- (cyclic carbonate) | n$_D^{20}$ 1.5578 |
| 40 | 4-Cl-C$_6$H$_4$- | -CH$_2$-CH$_2$- | -CH(CH$_2$Cl)-O-C(=O)-O- (cyclic carbonate) | n$_D^{20}$ 1.5492 |
| 41 | 4-F$_3$CO-C$_6$H$_4$- | -CH$_2$-CH$_2$- | -C(=N-O-4-Cl-C$_6$H$_4$)- | n$_D^{22}$ 1.5296 |
| 42 | 4-F$_3$CO-C$_6$H$_4$- | -CH$_2$-CH$_2$- | -C(=N-O-CH$_2$-4-NO$_2$-C$_6$H$_4$)- | n$_D^{22}$ 1.5370 |
| 43 | 4-F$_3$CO-C$_6$H$_4$- | -CH$_2$-CH$_2$- | -C(=N-O-CH$_2$-CH$_2$-C$_6$H$_5$)- | n$_D^{20}$ 1.5092 |
| 44 | 4-F$_3$CO-C$_6$H$_4$- | -CH$_2$-CH$_2$- | -C(=N-O-CH$_2$-2,6-Cl$_2$-C$_6$H$_3$)- | n$_D^{22}$ 1.5110 |
| 45 | 4-F$_3$CO-C$_6$H$_4$- | -CH$_2$-CH$_2$- | -C(=N-O-CH$_2$-2-Cl-C$_6$H$_4$)- | n$_D^{23}$ 1.5217 |
| 46 | 4-Cl-C$_6$H$_4$- | -CH$_2$-CH$_2$- | -C(=N-O-CH$_2$-4-Cl-C$_6$H$_4$)- | n$_D^{23}$ 1.5498 |
| 47 | 4-Cl-C$_6$H$_4$- | -CH$_2$-CH$_2$- | -C(=N-O-CH$_2$-4-NO$_2$-C$_6$H$_4$)- | n$_D^{23}$ 1.5632 |
| 48 | 4-Cl-C$_6$H$_4$- | -CH$_2$-CH$_2$- | -C(=N-O-CH$_2$-CH$_2$-C$_6$H$_5$)- | n$_D^{23}$ 1.5529 |
| 49 | 4-Cl-C$_6$H$_4$- | -CH$_2$-CH$_2$- | -C(=N-O-CH$_2$-2,6-Cl$_2$-C$_6$H$_3$)- | n$_D^{23}$ 1.5731 |

TABLE 1-continued

| Example No. | Ar | A | X | Physical properties |
|---|---|---|---|---|
| 50 | 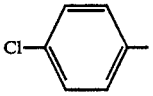 Cl—⌬— | —CH₂—CH₂— | $\overset{\underset{\|}{N-O-CH_2}}{-C-}$ ⌬—Cl | $n_D^{23}$ 1.5575 |
| 51 | F₃CO—⌬— | —CH₂—CH₂— | $\overset{\underset{\|}{N-OCH_3}}{-C-}$ | Mp 124° C. |
| 52 | F₃CO—⌬— | —CH₂—CH₂— | $\overset{\underset{\|}{N-OCH_3}}{-C-}$ | Mp 224° C. $\left[ \times \;\;\underset{SO_2}{\underset{\|}{\overset{O}{\overset{\|}{\bigcirc}}}}NH \right]$ |
| 53 | F₃CO—⌬— | —CH₂—CH₂— | $\overset{\underset{\|}{N-OCH_3}}{-C-}$ | Mp 110° C. $\left[ \times \; CH_3-⌬-SO_3H \right]$ |

Use Examples

In the following use examples, the compounds listed below have been employed as comparison substances:

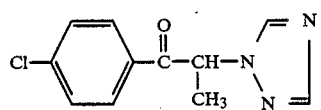

(1-(4-chlorophenyl)-2-(1,2,4-triazol-1-yl)-propan-1-one  (A)

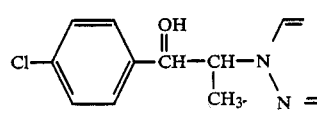

1-(4-chlorophenyl)-2-(1,2,4-triazol-1-yl)-propan-1-ol  (B)
(both disclosed in DE-OS (German Published Specification No. 2,431,407)

Example A

*Pyrenophora teres* test (barley)/protective
Solvent: 100 parts by weight of dimethylformamide
Emulsifier: 0.25 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a conidia suspension of Pyrenophora teres. The plants remain in an incubation cabin at 20° C. and 100% relative atmospheric humidity for 48 hours.

The plants are placed in a greenhouse at a temperature of about 20° C. and a relative atmospheric humidity of about 80%.

Evaluation is carried out 7 days after the inoculation.

In this test, the substances according to the invention given in Examples 7, 19, 21, 29, 32 and 33 show a considerably better activity than comparison substances (A) and (B).

Example B

*Leptosphaeria nodorum* test (wheat)/protective
Solvent: 100 parts by weight of dimethylformamide
Emulsifier: 0.25 parts by weight of alkyl aryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a conidia suspension of *Leptosphaeria nodorum*. The plants remain for 48 hours in an incubation cabin at 20° C. and 100% relative atmospheric humidity.

The plants are placed in a greenhouse at a temperature of about 15° C. and a relative atmospheric humidity of about 80%.

Evaluation is carried out 10 days after the inoculation.

In this test, the substances according to the invention given in Examples 7, 19, 20, 21, 29, 32 and 33 show a considerably better activity than comparison substances (A) and (B).

Example C

In order to determine the activity against fungi which are to be combated in the protection of materials, the minimum inhibitory concentrations (MIC) of active compounds according to the invention are determined.

Active compounds according to the invention are added, in concentrations of 0.1 mg/l to 5,000 mg/l, to an agar which is prepared using brewer's wort and peptone. When the agar has solidified, it is contaminated with pure cultures of test organisms. The agar is stored at 28° C. and 60 to 70% relative atmospheric humidity for 2 weeks, and the MIC is determined. MIC is the lowest concentration of active compound at which no growth whatsoever by the species of microbe used takes place.

In this test, the active compounds according to the invention given in Examples 1, 7 and 12 show MIC values of between 50 and 1,000 mg/l for *Aspergillus niger, Chaetomium globosum* and *Penicillium glaucum*.

It is understood that the specification and examples are illustrative but not limitative of the present invention and that other embodiments within the spirit and scope of the invention will suggest themselves to those skilled in the art.

What is claimed is:

1. A substituted triazole of the formula 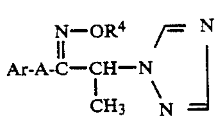 in which

Ar stands for aryl which has 6 to 10 carbon atoms and which can be monosubstituted or polysubstituted by identical or different substituents from the group consisting of halogen, cyano, nitro, in each case straight-chain or branched alkyl, alkoxy and alkylthio, each having 1 to 4 carbon atoms, in each case straight-chain or branched halogenalkyl, halogenoalkoxy and halogenoalkyhlthio, each having 1 to 4 carbon atoms and 1 to 9 identical or different halogen atoms, in each case straight-chain or branched alkoxycarbonyl and alkoximinoalkyl, each having 1 to 4 carbon atoms in the alkoxy moiety and 1 to 4 carbon atoms in the alkyl moiety, phenyl which is optionally monosubstituted or polysubstituted by identical or different substituents from the group consisting of halogen and straight-chain or branched alkyl having 1 to 4 carbon atoms, phenoxy which is optionally monosubstituted or polysubstituted by identical or different substituents from the group consisting of halogen and straight-chain or branched alkyl having 1 to 4 carbon atoms and by benzyloxy which is optionally monosubstituted or polysubstituted by identical or different substituents from the group consisting of halogen and straight-chain or branched alkyl having 1 to 4 carbon atoms, A stands for the group 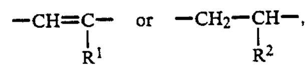 $R^1$ stands for hydrogen or for straight-chain or branched alkyl having 1 to 4 carbon atoms, $R^2$ stands for hydrogen or straight-chain or branched alkyl having 1 to 4 carbon atoms, $R^4$ stands for hydrogen, straight-chain or branched alkyl having 1 to 6 carbon atoms or stands for cycloalkyl having 3 to 7 carbon atoms, it being possible for each of the cycloalkyl radicals to be monosubstituted or polysubstituted by identical or different substituents from the group consisting of halogen, straight-chain or branched alkyl having 1 to 4 carbon atoms and straight-chain or branched halogenoalkyl having 1 to 4 carbon atoms and 1 to 9 identical or different halogen atoms, or stands for aralkyl having 6 to 10 carbon atoms in the aryl moiety and 1 to 4 carbon atoms in the straight-chain or branched alkyl moiety, it being possible for each of the alkyl radicals to be monosubstituted or polysubstituted by identical or different substituents from the group consisting of halogen, cyano, nitro, in each case straight-chain or branched alkyl, alkyloxy or alkylthio, each having 1 to 4 carbon atoms, in each case straight-chain or branched halogenoalkyl, halogenoalkoxy and halogenoalkythio, each having 1 to 4 carbon atoms and 1 to 9 identical or different halogen atoms, or stands for aryl having 6 to 10 carbon atoms, it being possible for each of the aryl radicals to be monosubstituted or polysubstituted by identical or different substituents from the group consisting of halogen, cyano, nitro, in each case straight-chain or branched alkyl, alkoxy or alkylthio, each having 1 to 4 carbon atoms, in each case straight-chain or branched halogenoalkyl, halogenoalkoxy and halogenoalkylthio, each having 1 to 4 carbon atoms and 1 to 9 identical or different halogen atoms, or an addition product thereof with an acid or metal salt.

2. A substituted triazole or addition product thereof according to claim 1, in which Ar stands for phenyl which can be monosubstituted disubstituted or trisubstituted by identical or different substituents from the group consisting of fluorine, chlorine, bromine, cyano, nitro, methyl, ethyl, n- or i-propyl, n-, i-, s- or t-butyl, methoxy, ethoxy, n- or i-propoxy, methylthio, trifluoromethyl, difluromethyl, fluorochloromethyl, difluorochloromethyl, trifluoromethoxy, diflurómethoxy, fluorothloromethoxy, difluorochloromethoxy, trifluoromethylthio, methoxycarbonyl, ethoxycarbonyl, methoximinomethyl, ethoximinomethyl, methoximinoethyl, ethoximinoethyl, phenyl which is optionally monosubstituted, disubstituted or trisubstituted by identical or different substituents from the group consisting of fluorine, chlorine, bromine, methyl and ethyl, phenoxy which is optionally nonsubstituted, disubstituted or trisubstituted by identical or different substituents from the grown consisting of fluorine, chlorine, bromine, methyl and ethyl, and benzyloxy which is optionally nonosubstituted, disubstituted or trisubstituted by identical or different substitutents from the group consisting of fluorine, chlorine, bromine, ethyl and ethyl, A stands for the groups

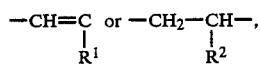

R¹ stands for hydrogen methyl, ethyl, n- or i-propyl and n-, i-, s- or t-butyl,

R² stands for hydrogen, methyl, ethyl, n- or i-propyl and n-, i-, s- or t-butyl and, R⁴ stands for hydrogen, methyl, ethyl, n- or i-propyl, n-, i-, s- or t-butyl, for cyclopropyl, cyclopentyl or cyclohexyl, each of which is optionally monosubstituted, disubstituted or trisubstituted by identical or different substituents from the group consisting of fluorine, chlorine, bromine, methyl, ethyl and trifluoromethyl, or for benzyl, phenethyl or phenyl, it being possible for each of the three abovementioned radicals to be monosubstituted, disubstituted or trisubstituted in the phenyl moiety by identical or different substituents from the group consisting of fluorine, chlorine, bromine, cyano, nitro, methyl, ethyl, n- or i-propyl, n-, i-, s- or t-butyl, methoxy, ethoxy, n- or i-propoxy, methylthio, trifluoromethyl trifluoromethoxy and trifluoromethylthio.

3. A substituted triazole or addition product thereof according to claim 1,
in which
Ar stands for phenyl which can be monsubstituted or disubstituted by identical or different substituents from the group consisting of fluorine, chlorine, bromine, cyano, methyl, ethyl, n- or i-propyl, n-, i-, s- or t-butyl, methoxy, ethoxy, n- or i-propoxy, methylthio, trifluoromethy, difluoromethyl, fluorochloromethyl, difluorochloromethyl, trifluoromethoxy, difluoromethoxy, fluorochloromethoxy, difluorochloromethoxy, trifluoromethylthio, methoximinomethyl, ethoximinomethyl methoximinoethyl and ethoximinoethyl, phenyl which is optionally monosubstituted or disubstituted by chlorine, phenoxy which is optionally monosubstituted or disubstituted by chlorine and by benzyloxy which is optionally monosubstituted or disubstituted by chlorine, A stands for the groups

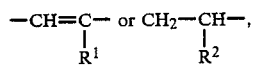

R¹ stands for hydrogen or methyl,
R² stands for hydrogen or methyl, and
R⁴ stands for hydrogen, methyl, ethyl, cyclohexyl, or benzyl, phenethyl or phenyl which are optionally nonosubstituted or disubstitutes by chlorine or nitro.

4. A substituted triazole or addition product thereof according to claim 1,
in which
Ar stands for phenyl which can be monosubstituted or disubstituted by identical or different substituents selected from the group consisting of fluorine, chlorine, methyl, trifluoromethyl, trifluoromethoxy and phenyl,
A stands for the groups

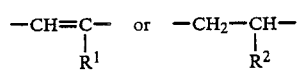

wherein
R¹ stands for hydrogen or methyl, and
R² stands for hydrogen or methyl, and
R⁴ stands for hydrogen, methyl, ethyl, phenyl which can be monosubstituted or disubstituted by identical or different substituents selected from the group consisting of fluorine, chlorine, methyl and trifluoromethyl, or represents benzyl or phenethyl each of which may be monosubstituted or disubstituted in the phenyl moiety by identical or different substituents selected from the group consisting of fluorine, chlorine, nitro and trifluoromethyl,
or an addition product thereof with an acid or metal salt.

5. A compound according to claim 1 wherein such compound is 1-(4-trifluoromethoxy-phenyl)-2-methyl-3-methoximino-4-(1,2,4-triazol-1-yl)-pent-1-ene of the formula

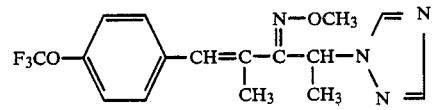

or an addition product thereof with an acid or metal salt.

6. A compound according to claim 1, wherein such compound is 1-(4-trifluoromethoxy-phenyl)-3-methoximino-4-(1,2,4-triazol-1-yl)-pentane of the formula

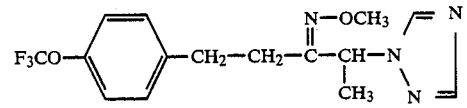

or an addition product thereof with an acid or metal salt.

7. A fungicidal composition comprising a fungicidally effective amount of a compound or addition product thereof according to claim 1 and an inert diluent.

8. A method of combating fungi which comprises applying to such fungi or to a fungus habitat a fungicidally effective amount of a compound or addition product thereof according to claim 1.

9. The method according to claim 8, wherein such compound is
1-(4-trifluoromethoxy-phenyl)-2-methyl-3-methoximino-4-(1,2,4-triazol-1-yl)-pent-1-ene, or
1-(4-trifluoromethoxy-phenyl)-3-methoximino-4-(1,2,4-triazol-1-yl)-pentane,
or an addition product thereof with an acid or metal salt.

* * * * *

UNITED STATES PATENT AND TRADEMARK OFFICE
CERTIFICATE OF CORRECTION

PATENT NO. : 4,962,118

DATED : October 9, 1990

INVENTOR(S) : Kleefeld et al.

It is certified that error appears in the above-identified patent and that said Letters Patent is hereby corrected as shown below:

Col. 55, line 55     Delete " halogenalkyl " and substitute -- halogenoalkyl --

Col. 56, line 64     Delete " fluorothloremethoxy " and substitute -- fluorochloromethoxy --

Col. 57, lines 4 & 7-8     Delete " nonsubstituted " and substitute -- monosubstituted --

Col. 57, line 10     Delete " ethyl " and substitute -- methyl --

Col. 57, line 21     After " butyl " delete " and, " and substitute -- , and --

Col. 57, line 67     Delete " nonosubstituted or disubstitutes " and substitute -- monosubstituted or disubstituted --

Signed and Sealed this

Twentieth Day of July, 1993

Attest:

MICHAEL K. KIRK

*Attesting Officer*     Acting Commissioner of Patents and Trademarks